US005766888A

United States Patent [19]
Sobol et al.

[11] Patent Number: 5,766,888
[45] Date of Patent: *Jun. 16, 1998

[54] DETECTION OF CARCINOMA METASTASES BY NUCLEIC ACID AMPLIFICATION

[75] Inventors: Robert E. Sobol, La Jolla; Mark R. Green, San Diego; Ernest S. Kawasaki, Richmond, all of Calif.

[73] Assignees: Roche Molecular Systems, Inc., Branchburg, N.J.; The University of California, Oakland, Calif.

[ * ] Notice: The term of this patent shall not extend beyond the expiration date of Pat. No. 5,543,296.

[21] Appl. No.: 454,720

[22] Filed: May 31, 1995

Related U.S. Application Data

[63] Continuation of Ser. No. 357,565, Dec. 16, 1994, Pat. No. 5,543,296, which is a continuation of Ser. No. 96,110, Jul. 22, 1993, abandoned, which is a continuation of Ser. No. 720,061, Jun. 26, 1991, abandoned.

[51] Int. Cl.$^6$ .............. C12P 19/34; C12Q 1/68; C07H 21/04; C12N 15/00
[52] U.S. Cl. ............. 435/91.2; 435/6; 435/91.1; 536/23.1; 536/24.31; 536/24.33; 536/25.3; 935/77; 935/78
[58] Field of Search ............. 435/6, 91.1, 91.2, 435/91.5, 270, 183; 436/94; 536/23.1, 23.5, 24.31, 24.33, 25.3; 935/77, 78

[56] References Cited

U.S. PATENT DOCUMENTS

| 4,683,195 | 7/1987 | Mullis et al. | 435/6 |
| 4,965,188 | 10/1990 | Mullis et al. | 435/6 |
| 5,085,983 | 2/1992 | Scanlon | 435/6 |
| 5,543,296 | 8/1996 | Sobol et al. | 435/6 |

FOREIGN PATENT DOCUMENTS

| 8908717 | 9/1989 | WIPO . |
| 9109944 | 7/1991 | WIPO . |

OTHER PUBLICATIONS

Henthu et al., *Biochemical and Biophysical Research Communications* vol. 160, No. 2, pp. 903–910, Apr. 28, 1989.
Spindel et al., *Proc. Natl. Acad. Sci. USA* vol. 83, No. 1, pp. 19–23, Jan. 1986.
Canon et al., *Eur. J. Cancer Clin Oncol.* vol. 24, No. 2, pp. 147–150, 1988.
Jonas et al., *Proc. Natl. Acad. Sci. USA*, vol. 82, pp. 1994–1998, Apr. 1 1985.
Edhioke et al., *The Embo Journal*, vol. 4, No. 3, pp. 715–724, 1985.
Perez et al., *The Journal of Immunology*, vol. 142, No. 10 pp. 3662–3667, May 15, 1989.
Wang et al., 1979, "Purification of Human Prostate Specific Antigen" Investigative Urology 17(2):159–163.
Nadji et al., Sep., 1981, "Prostatic–Specific Antigen: An Immunohistologic Marker for Prostatic Neoplasms" Cancer 48:1229–1232.

Papsidero et al., Jan., 1981, "Prostate Antigen: A Marker for Human Prostate Epithelial Cells" JNCI 66(1):37–42.
Wang et al., 1981, "Prostate Antigen: A New Potential Marker for Prostatic Cancer" The Prostate 2:89–96.
Shaller et al., 1987, "Isolation Characterization and Amino–Acid Sequence of Gamma–Seminoprotein, a Glycoprotein from Human Seminal Plasma" Eur. J. Biochem. 170:111–120.
Stamey et al., May, 1989, "Prostate Specific Antigen in the Diagnosis and Treatment of Adenocarcinoma of the Prostate. I. Untreated Patients" J. Urol. 141: 1070–1075.
Stamey et al., May, 1989, "Prostate Specific Antigen in the Diagnosis and Treatment of Adenocarcinoma of the Prostate. II. Radical Prostatectomy Treated Patients" J. Urol. 141:1076–1083.
Hamdy et al., 1992, "Circulating Prostate Specific Antigen–Positive Cells Correlate with Metastatic Prostate Cancer" British J. Urol. 69:392–396.
Sobol et al., 1982, "Use of Immunoglobulin Light Chain Analysis to Detect Bone Marrow Involvement in B–Cell Neoplasms" Clinical Immunology and Immunopathology 24:139–144.
Sobol et al., 1985, "Applications and Limitations of Peripheral Blood Lymphocyte Immunoglobuin Light Chain Analysis in the Evaluation of Non–Hodgkin's Lymphoma" Cancer 56:2005–2010.
Sobol et al., 1986, "A Novel Monclonal Antibody–Defined Antigen Which Distinguishes Human Non–Small Cell From Small Cell Lung Carcinomas" Cancer Research 46:4746–4750.
Sobol et al., 1987, "Elevated Serum Chromogranin A Concentrations in Small–Cell Lung Carcinoma" Ann. Intern. Med. 105:698–700.
Canon et al., 1988, "Immunodetection of Small Cell Lung Cancer Metastases in Bone Marrow Using Three Monoclonal Antibodies" Eur. J. Cancer Clin. Oncol. 24:147–150.
Berendsen et al., 1988, "Detection of Small Cell Lung Cancer Metastases in Bone Marrow Aspirates Using Monoclonal Antibody Directed Against Neuroendocrine Differentiation Antigen" J. Clin. Pathol. 41:273–276.
Stahl et al., 1985, "Detection of Bone Marrow Metastasis in Small–Cell Lung Cancer by Monoclonal Antibody" J. Clin. Oncol. 3(4):455–461.

(List continued on next page.)

*Primary Examiner*—Bradley L. Sisson
*Attorney, Agent, or Firm*—George W. Johnston; Dennis P. Tramaloni; Douglas A. Petry

[57] ABSTRACT

Methods are provided for detecting carcinoma metastases in selected body tissues and fluids. These methods offer greater than 1,000-fold enhanced sensitivity compared to prior standard diagnostic methods. In one embodiment of the invention, target carcinoma associated nucleic acid sequences are identified for detecting minimal residual disease in lung carcinomas. The methods utilize nucleic acid amplification techniques, preferably, the polymerase chain reaction.

5 Claims, No Drawings

OTHER PUBLICATIONS

Wright et al., 1987, "Gene Rearrangements as Markers of Clonal Variation and Minimal Residual Disease in Acute Lumphoblastic Leukemia" J. Clin. Oncol. 5:735–741.

Van Brunt, 1990, "Amplifying Genes: PCR and Its Alternatives" Bio/Technology 8:291–293.

Fey et al., 1991, "The Polymerase Chain Reaction: A New Tool Detection of Minimal Residual Disease In Haematological Malignancies" Eur. J. Cancer 27(1):89–94.

Bumol et al., 1988, "Characterization of the Human Tumor and Normal Tissue Reactivity of the KS1/4 Monoclonal Antibody" Hybridoma 7(4):407–415.

Perez and Walker, 1990, "Isolation and Characterization of a cDNA Encoding the KS1/4 Epithelial Carcinoma Marker" J. Immunol. 142(10):3662–3667.

Kayser et al., 1988, "Expression of Neuroendocrine Markers (Neuronspecific Enolase, Synaptophysin and Bombesin) in Carcionoma of the Lung" Pathology Research and Practice 183(4):412–417.

Spindel et al., 1986, "Two Prohormones for Gastrin–Releasing Peptide are Encoded by Two mRNAs Differing by 19 Nucleotides" Proc. Natl. Acad. Sci. USA 83:19–23.

Gazdar et al., 1988, "Expression of Neuroendocrine Cell Markers L–Dopa Decarboxylase, Chromogranin A, and Dense Core Granules in Human Tumors of Endocrine and Nonendocrine Origin" Cancer Research 48:4078–4082.

Suva, 1989, "Structure of the 5' Flanking Region of the Gene Encoding Human Parathyroid–Hormone–Related Protein (PTHrP)" Gene 77(1):95–105.

Martin et al., 1989, "Parathyroid Hormone–Related Protein: Isolation, Molecular Cloning, and Mechanism of Action" Recent Progress in Hormone Research 45:467–506.

Jonas et al., 1985, "Alternative RNA Processing Events in Human Calcitonin/Calcitonin Gene–Related Peptide Gene Expression" Proc. Natl. Acad. Sci. USA 82:1994–1998.

Edbrooke et al., 1985, "Expression of the Human Calcitonin/CGRP Gene in Lung and Thyroid Carcinoma" EMBO J. 4(3):715–724.

Russell et al., 1990, "Ectopic Hormone Production by Small Cell Undifferentiated Carcinomas" Mol. Cell Endocrin. 71:1–12.

Knoecki et al., 1987, "The Primary Structure of Human Chromogranin A and Pancreastatin" JBC 262:17026–17030.

Mohr et al., 1985, "Expression of the Vasopressin and Oxytocin Genes in Human Hypothalami" FEBS Letters 193(1):12–16.

North et al., 1988, "Neurophysins as Tumor Markers for Small Cell Carcinoma of the Lung" Cancer 62(7):1343–1347.

Kibbelaar et al., 1989, "Expression of the Embryonal Neural Cell Adhesion Molecule N–Cam in Lung Carcinoma. Diagnostic Usefulness of Monoclonal Antibody 735 for the Distinction Between Small Cell Lung Cancer and Non–Small Cell Lung Cancer" J. Pathology 159:23–28.

Yu et al., 1991, "Coexpression of Different Antigenic Markers on Moieties that Bear CA 125 Determinants" Cancer Res. 51(2):468–475.

Tailor et al., 1990, "Nucleotide Sequence of Human Prostatic Acid Phosphatase Determined From a Full–Length cDNA Clone" Nucleic Acids Research 18(16):4928.

Henttu and Vihko, 1989, "cDNA Coding for the Entire Human Prostate Specific Antigen Shows High Homologies to the Human Tissue Kallikrein Genes" Biochemical and Biophys Res. Comm. 160(2):903–910.

Estin et al., 1989, "Transfected Mouse Melanoma Lines That Express Various Levels of Human Melanoma–Associated Antigen p.97", J.Natl. Cancer Instit. 81(6):445–446.

Vijayasardahi et al., 1990, "The Melanoma Antigen gp75 is the Human Homologue of the Mouse b (Brown) Locus Gene Product" J. Experimental Medicine 171(4):1375–1380.

Natali et al., 1987, "Immunohistochemical Detection of Antigen in Human Primary and Metastatic Melanomas by the Monoclonal Antibody 140.240 and Its Possible Prognostic Significance" Cancer 59:55–63.

Darnell et al., 1990, "Characteristics of Tumor Cells" Molecular Cell Biology, second edition, W.H. Freeman and Co., New York, pp. 956–957.

Lipson and Baserga, 1989, "Transcriptional Activity of the Human Thymidine Kinase Gene Determined by a Method Using the Polymerase Chain Reaction and an Intron–Specific Probe" Proc. Natl. Acad. Sci. USA 86:9774–9777.

Cohen et al., 1984, "Selective Localization of the Parathyroid Secretory Protein–I/Adrenal Medulla Chromogranin A Protein Family in a Wide Variety of Endocrine Cells of the Rat" Endocrinology 114(6):1963–1974.

Wilbur and Lipman, Feb., 1983, "Rapid Similarity Searches of Nucleic Acid and Protein Data Banks" Proc. Natl. Acad. Sci. USA 80:726–730.

Stratagene Catalog, 1988, p. 39.

Helman et al., 1988, "Molecular Cloning and Primary Structure of Human Chromogranin A (Secretory Protein I) cDNA" J. Biological Chemistry 263(23):11559–11563.

Kawaswaki et al., Aug, 1988, "Diagnosis of Chronic Myeloid and Acute Lymphocytic Leukemias by Detection of Leukemia–Specific mRNA Sequences Amplfiied In Vitro" Proc. Natl. Acad. Sci. USA 85:5698–5702.

SEQUENCE LISTING ( 1 ) GENERAL INFORMATION:

( i i i ) NUMBER OF SEQUENCES: 42

( 2 ) INFORMATION FOR SEQ ID NO: 1:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 1:

GGTGCAGGAC TATGTGCAGA TG        22

( 2 ) INFORMATION FOR SEQ ID NO: 2:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 2:

GTCGCTGGAC ATATCCCTTT TC        22

( 2 ) INFORMATION FOR SEQ ID NO: 3:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 3:

GGTGGGCACA AAGTTGTTCT TC        22

( 2 ) INFORMATION FOR SEQ ID NO: 4:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 4:

GTTGAGGTCA TCTCCGACAC AC 22

( 2 ) INFORMATION FOR SEQ ID NO: 5:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 5:

CTCTGGTTCT CAAGAACCTC TG 22

( 2 ) INFORMATION FOR SEQ ID NO: 6:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 6:

CATCCTTGGA TGATGGCTCT TC 22

( 2 ) INFORMATION FOR SEQ ID NO: 7:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 7:

GACCGTGCTG ACCAAGATGT AC 22

( 2 ) INFORMATION FOR SEQ ID NO: 8:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 8:

GGTGGTTTCT GTTCTCCTTT GC 22

( 2 ) INFORMATION FOR SEQ ID NO: 9:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 9:

GAACCTGGAG CAGAGAGTCT AC 22

( 2 ) INFORMATION FOR SEQ ID NO: 10:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 10:

GTCTGTGAAA ACTACAAGCT GG      22

( 2 ) INFORMATION FOR SEQ ID NO: 11:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 11:

CCCTTCAGGT TTTGCTCTTC TC      22

( 2 ) INFORMATION FOR SEQ ID NO: 12:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 12:

GTCCTTGTCT GTTCTTCTGA CC      22

( 2 ) INFORMATION FOR SEQ ID NO: 13:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 13:

CCGCGTGCTA CTTCCAGAAC TG      22

( 2 ) INFORMATION FOR SEQ ID NO: 14:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 14:

CAGGTAGTTC TCCTCCTGGC AG      22

( 2 ) INFORMATION FOR SEQ ID NO: 15:

( i ) SEQUENCE CHARACTERISTICS:
        ( A ) LENGTH: 22 bases ( B ) TYPE: nucleic acid
            ( C ) STRANDEDNESS: single
            ( D ) TOPOLOGY: linear ( i i ) MOLECULE TYPE: Other Nucleic Acid ( x i ) SEQUENCE DESCRIPTION: SEQ ID NO: 15:

GCTCTCGTCG TTGCAGCAAA CG                                                            2 2

( 2 ) INFORMATION FOR SEQ ID NO: 16:

( i ) SEQUENCE CHARACTERISTICS:
            ( A ) LENGTH: 22 bases
            ( B ) TYPE: nucleic acid
            ( C ) STRANDEDNESS: single
            ( D ) TOPOLOGY: linear ( i i ) MOLECULE TYPE: Other Nucleic Acid ( x i ) SEQUENCE DESCRIPTION: SEQ ID NO: 16:

GCTTTGTGAA GGTGCTGCAA TG                                                            2 2

( 2 ) INFORMATION FOR SEQ ID NO: 17:

( i ) SEQUENCE CHARACTERISTICS:
            ( A ) LENGTH: 22 bases
            ( B ) TYPE: nucleic acid
            ( C ) STRANDEDNESS: single
            ( D ) TOPOLOGY: linear ( i i ) MOLECULE TYPE: Other Nucleic Acid ( x i ) SEQUENCE DESCRIPTION: SEQ ID NO: 17:

GTACTCGAAC TCGACCTCGA TG                                                            2 2

( 2 ) INFORMATION FOR SEQ ID NO: 18:

( i ) SEQUENCE CHARACTERISTICS:
            ( A ) LENGTH: 22 bases
            ( B ) TYPE: nucleic acid
            ( C ) STRANDEDNESS: single
            ( D ) TOPOLOGY: linear ( i i ) MOLECULE TYPE: Other Nucleic Acid ( x i ) SEQUENCE DESCRIPTION: SEQ ID NO: 18:

GACAAAGAAT TCGGCTGACG AG                                                            2 2

( 2 ) INFORMATION FOR SEQ ID NO: 19:

( i ) SEQUENCE CHARACTERISTICS:
            ( A ) LENGTH: 20 bases
            ( B ) TYPE: nucleic acid
            ( C ) STRANDEDNESS: single
            ( D ) TOPOLOGY: linear ( i i ) MOLECULE TYPE: Other Nucleic Acid ( x i ) SEQUENCE DESCRIPTION: SEQ ID NO: 19:

CTGAGTACTT GCATGCTGGG                                                               2 0

( 2 ) INFORMATION FOR SEQ ID NO: 20:

( i ) SEQUENCE CHARACTERISTICS:
            ( A ) LENGTH: 20 bases
            ( B ) TYPE: nucleic acid
            ( C ) STRANDEDNESS: single
            ( D ) TOPOLOGY: linear ( i i ) MOLECULE TYPE: Other Nucleic Acid (xi) SEQUENCE DESCRIPTION: SEQ ID NO: 20:

GACACTGCCA CCTGTGTGAC                    20

(2) INFORMATION FOR SEQ ID NO: 21:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO: 21:

GACACTCCGA GGAGATGAAC                    20

(2) INFORMATION FOR SEQ ID NO: 22:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO: 22:

CACAGGGGAG TCTTCTTCTG                    20

(2) INFORMATION FOR SEQ ID NO: 23:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO: 23:

CTGGCTGCCA AATGTTTGGT G                    21

(2) INFORMATION FOR SEQ ID NO: 24:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO: 24:

GACCTGGAGC TGAGACAGTG                    20

(2) INFORMATION FOR SEQ ID NO: 25:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO: 25:

CCAACAAGAC CGAGAGTGAC                    20

( 2 ) INFORMATION FOR SEQ ID NO: 26:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 26:

GATGATGATA TCGCCGCGCT C                                    2 1

( 2 ) INFORMATION FOR SEQ ID NO: 27:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 27:

CATGTCGTCC CAGTTGGTGA C                                    2 1

( 2 ) INFORMATION FOR SEQ ID NO: 28:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 28:

CTCTCATATC AACCCGAGTG TCTC                                2 4

( 2 ) INFORMATION FOR SEQ ID NO: 29:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 29:

CCTCTGCACT ATGTCACTGA TTTC                                2 4

( 2 ) INFORMATION FOR SEQ ID NO: 30:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 30:

CCTTCCTGGG CATGGAGTCC TG                                  2 2

( 2 ) INFORMATION FOR SEQ ID NO: 31:

( i ) SEQUENCE CHARACTERISTICS:
        ( A ) LENGTH: 21 bases ( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 31:

```
GGAGCAATGA TCTTGATCTT C                                                      21
```

( 2 ) INFORMATION FOR SEQ ID NO:32:

( i ) SEQUENCE CHARACTERISTICS:
        ( A ) LENGTH: 894 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 32:

```
GCGACTTTTG CCGCAGCTCA GGAAGAATGT GTCTGTGAAA ACTACAAGCT GGCCGTAAAC    60
TGCTTTGTGA ATAATAATCG TCAATGCACG TGTACTTCAG TTGGTGCACA AAATACTGTC   120
ATTTGCTCAA AGCTGGCTGC CAAATGTTTG GTGATGAAGG CAGAAATGAA TGGCTCAAAA   180
CTTGGGAGAA GAGCAAAACC TGAAGGGGCC CTCCAGAACA ATGATGGGCT TTATGATCCT   240
GACTGCGATG AGAGCGGGCT CTTTAAGGCC AAGCAGTGCA ACGGCACCTC CACGTGCTGG   300
TGTGTGAACA CTGCTGGGGT CAGAAGAACA GACAAGGACA CTGAAATAAC CTGCTCTGAG   360
CGAGTGAGAA CCTACTGGAT CATCATTGAA CTAAAACACA AGCAAGAGA  AAAACCTTAT   420
GATAGTAAAA GTTTGCGGAC TGCACTTCAG AAGGAGATCA CAACGCGTTA TCCACTGGAT   480
CCAAAATTTA TCACGAGTAT TTGTATGAG  AATAATGTTA TCACTATTGA TCTGGTTCAA   540
AATTCTTCTC AAAAAACTCA GAATGATGTG GACATAGCTG ATGTGGCTTA TTATTTTGAA   600
AAAGATGTTA AGGTGAATC  CTTGTTTCAT TCTAAGAAAA TGGACCTGAC AGTAAATGGG   660
GAACAACTGG ATCTGGATCC TGGTCAAACT TTAATTTATT ATGTTGATGA AAAAGCACCT   720
GAATTCTCAA TGCAGGGTCT AAAAGCTGGT GTTATTGCTG TTATTGTGGT TGTGGTGATG   780
GCAGTTGTTG CTGGAATTGT TGTGCTGGTT ATTCCAGAA  AGAAGAGAAT GGCAAAGTAT   840
GAGAAGGCTG AGATAAAGGA GATGGGTGAG ATGCATAGGG AACTCAATGC ATAA         894
```

( 2 ) INFORMATION FOR SEQ ID NO:33:

( i ) SEQUENCE CHARACTERISTICS:
        ( A ) LENGTH: 223 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

```
CAGCTGAGAG AGTACATCAG GTGGGAAGAA GCTGCAAGGA ATTTGCTGGG TCTCATAGAA    60
GCAAAGGAGA ACAGAAACCA CCAGCCACCT CAACCCAAGG CCTTGGGCAA TCAGCAGCCT   120
TCGTGGGATT CAGAGGATAG CAGCAACTTC AAAGATGTAG GTTCAAAAGG CAAAGTTGGT   180
AGACTCTCTG CTCCAGGTTC TCAACGTGAA GGAAGGAACC CCC                    223
```

( 2 ) INFORMATION FOR SEQ ID NO:34:

( i ) SEQUENCE CHARACTERISTICS:
        ( A ) LENGTH: 204 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:34:

| | | | | | |
|---|---|---|---|---|---|
| CAGCTGAGAG | AGTACATCAG | GTGGGAAGAA | GCTGCAAGGA | ATTTGCTGGG | TCTCATAGAA | 60 |
| GCAAAGGAGA | ACAGAAACCA | CCAGCCACCT | CAACCCAAGG | CCTTGGGCAA | TCAGCAGCCT | 120 |
| TCGTGGGATT | CAGAGGATAG | CAGCAACTTC | AAAGATTTGG | TAGACTCTCT | GCTCCAGGTT | 180 |
| CTCAACGTGA | AGGAAGGAAC | CCCC | | | | 204 |

(2) INFORMATION FOR SEQ ID NO:35:

(i) SEQUENCE CHARACTERISTICS:
(A) LENGTH: 1990 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:35:

| | | | | | |
|---|---|---|---|---|---|
| AAAGGATGGG | TTAGACTCCC | GACCATGAGT | GAAAAGGGCC | GTGTGCGTGC | TCCAGGAGTG | 60 |
| TCGGTCCCCC | TCTGCAATTC | AAAAGGGGGA | TCTCTCCTGT | GCGCGGGTTT | TTTGGGACCG | 120 |
| GCTCCAGATG | TCTCCCAGCG | AGTTCTGAAA | CAGCAAAAAG | TGCAATTTAG | ATATGAAATC | 180 |
| TGGAACTGTT | TTTGTTCTTC | TAAGCAAAAG | ATCTCCCTCT | CTCTAGCCGA | TGCTCCCCAC | 240 |
| TCAGTTCATC | CCGGGAATGG | GCCAGGGAGG | AAGGTTCTCA | TGCATCGCCC | CGAGCTGCCA | 300 |
| GGCGACCTTC | GGGCTCCTTA | AATTCACAGG | CCAACAGCCC | GCGTCCTCTC | CGCGCAGGCT | 360 |
| CCCGGTTGCC | CGCGGTCCCC | GGCCCAGCTC | CTTGGCCTCC | TCTCGTCGG | TCCGCCCCTG | 420 |
| GTGGTCTTGG | CGCCCGCTCG | TCCAGCTCGG | CGCGCCGGGG | ACCGCCGGCT | GCCCGGGGCA | 480 |
| GTCCGCACGC | CCTCGGGGAT | CTCGGCTCCC | GGATCCGCCG | CGCCGGCAGG | AGCCGGCCGG | 540 |
| GCCTGGAGGG | AGCAAGCGGA | TCGCCACGCC | CCCGGCACGG | ATGGGCGACA | GGGCCGGGCT | 600 |
| CCGGGGTGGG | GCTCGGCAGA | GCTCCTGACA | GCTCCGGGGT | CGGCAGCGGG | GAGGGGGGAG | 660 |
| CTCCGCCGCT | CGCCGCTCAT | TCCCGGCTCG | GGGCTCCCCT | CCACTCGCTC | GGGCGGCGCG | 720 |
| GGGCCCGTTG | CGCCGCCCGT | CGCGCCCCCG | CCCCCGCGC | GCCCGCCCGC | CAGCCCGCCC | 780 |
| GTGCCCGCTT | CGCCCCGCGC | GCGTTCCTAG | GGCGCCACCT | CTTTGCGACT | AGCTCACTTC | 840 |
| TAGCAGGTTT | GCCTCGGAGC | GTGTGAACAT | TCCTCCGCTC | GGTTTTCAAC | TCGCCTCCAA | 900 |
| CCTGCGGCCC | GGCCAGCATG | TCTCCGCCCG | TGAAGCGGGC | TCGCCTCCCT | GGCTCCGGCT | 960 |
| GCCACTAACG | ACCCGCCCTC | GCCCGACCTG | GCCCTCCTGA | TCGACGACAC | ACGCACTTGA | 1020 |
| AACTTGTTCT | CAGGGTGTGT | GGAATCAACT | TTCCGGAAGC | AACCAGCCCA | CCAGAGGAGG | 1080 |
| TAGACAGACA | GCTATGTATA | TATATGTGGG | TTTCGCTACA | AGTGGCTCTG | GAACGAAAGG | 1140 |
| GCCTGGTTCG | CAAAGAAGCT | GACTTCAGAG | GGGGAAACTT | TCTTCTTTTA | GGAGGCGGTT | 1200 |
| AGCCCTGTTC | CACGAACCCA | GGAGAACTGC | TGGCCAGATT | AATTAGACAT | TGCTATGGGA | 1260 |
| GACGTGTAAA | CACAATACTT | ATCATTGATG | CATATATAAA | ACCATTTTAT | TTCGCTATT | 1320 |
| ATTTCAGAGG | AAGCGCCTCT | GATTTGTTTC | TTTTTTCCCT | TTTGCTCTT | TCTGGCTGTG | 1380 |
| TGGTTTGGAG | AAAGCACAGT | TGGAGTAGCC | GGTTGCTAAA | TAAGTAAGTG | CTGAGAGGCT | 1440 |
| CCAGAGAAAT | TTTTTTTCTT | TTCAACTTGG | GAGATGCCCT | TGATGTTGAA | GAGGCTTTTT | 1500 |
| GAGAGCGGGC | TAAAAAGGGG | GAGCGGAGTA | GTGCGGGGAG | ATGGAGAGTC | CTGACTGACA | 1560 |

-continued

```
CCTCGGGTCC CATTCCCTTC TGTTGCAGGT CCCGAGCGCG AGCGGAGACG ATGCAGCGGA      1620

GACTGGTTCA GCAGTGGAGC GTCGCGGTGT TCCTGCTGAG CTACGCGGTG CCCTCCTGCG      1680

GGCGCTCGGT GGAGGGTCTC AGCCGCCGCC TGTAAGTCCC CCATCCTCCC CAGGGCGCCG      1740

GGTTGGGGAG GCCAGGGGGA GGGGCTGCCA AGCTGGGATG CTGCCGAGGC GTTGCAGCGG      1800

TCACCGATCG TCCTTGCCCG GGTTAGGGAG AGGGACCATC CCGCATACCT GCCGGGCCTG      1860

AGCCGTTCTC AAACTTGGCA GGAGAACTGG TTGATCTTCA ACCGGAGACA GGCAAGAGAG      1920

AGACTTTATG TGTGTTTCCA TAAGAGGGAG CTTTCACAGA ATCTCTTCTA GGGAAAGATC      1980

CTTGCCTCTA                                                              1990
```

( 2 ) INFORMATION FOR SEQ ID NO:36:

( i ) SEQUENCE CHARACTERISTICS:
        ( A ) LENGTH: 1833 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

```
GTCCTGCTGG CTGCACTGGT GCAGGACTAT TGTCAGATGA AGGCCAGTGA GCTGGAGCAG      60

GAGCAAGAGA GAGAGGGCTC CAGCCTGGAC AGCCCCAGAT CTAAGCGGTG CGGTAATCTG      120

AGTACTTGCA TGCTGGGCAC ATACACGCAG GACTTCAACA AGTTTCACAC GTTCCCCCAA      180

ACTGCAATTG GGGTTGGAGC ACCTGGAAAG AAAAGGGATA TGTCCAGCGA CTTGGAGAGA      240

GACCATCGCC CTCATGTTAG CATGCCCCAG AATGCCAACT AAACTCCTCC CTTTCCTTCC      300

TAATTTCCCT TCTTGCATCC TTCCTATAAC TTGATGCATG TGGTTTGGTT CCTCTCTGGT      360

GGCTCTTTGG GCTGGTATTG GTGGCTTTCC TTGTGGCAGA GGATGTCTCA AACTTCAGAT      420

GGGAGGAAAG AGAGCAGGAC TCACAGGTTG GAAGAGAATC ACCTGGGAAA ATACCAGAAA      480

ATGAGGGCCG CTTTGAGTCC CCCAGAGATG TCATCAGAGC TCCTCTGTCC TGCTTCTGAA      540

TGTGCTGATC ATTTGAGGAA TAAAATTATT TTTCCCCAAA GATCTGAGCT GTGGTGGTCA      600

TTGCTCTGAT CTATGTCCCA GGCTTCATAG TGTCTAAGAC CTATGCTTAG AAATAGCCTT      660

AACCCTAGGC TAGCTGGACA GAGGATATGG TGGGTGGTCC CTTTGACCAA GCTCAAGCAG      720

GAAGAACAGG GGTCCTAAGG AGCAGGTAAG CACCTCTAGG ACTTGATGCT GCAAACTCCG      780

CTCCTCTTCC AGGTAAGACT GAGGAATTTT TTATTTTCCT AAGAAAGGGT ATTTGGTGCC      840

CGTGACTGGG GTGTAGATTT TATAGTCCTT TGTGAATGGG GCTGGGTGTG GGACCATAAT      900

TCACTCCAGT GTCATAAACC TCCGCTTTGA TTTTTAGTTA ATTTATACAG GAAAGATTGG      960

CTGTTACTGC TCCACATTCC ATAGCCAGTC ATCCAGAGTC ACCTTGGGTT TCTGACACCC      1020

CTGGGAATAT CTATGGGGAG TGATCATGGC ATTTTCCCTA ATGGCCTTGT GATTTCTGC      1080

TCTGATAATT GTGTTTAGGA GAAACACTTA AAGTTAATTG GTGCCTTTCA GCACAGCAAC      1140

TTTACCATGA AGGTCCCATG GGGCTGACCT CTCTCCCAGC CTCTCACTCA CAGATCTTCT      1200

CTTCTTTCTC CATCCTGCAA ATCATCATTG CCCAGAAGAG AGCCTGTGAC ACTGCCACCT      1260

GTGTGACTCA TCGGCTGGCA GGCTTGCTGA GCAGATCAGG GGGTGTGGTG AAGAACAACT      1320

TTGTGCCCAC CAATGTGGGT TCCAAAGCCT TGGCAGGCG CCGCAGGGAC CTTCAAGCCT      1380

GAGCAGCTGA ATGATCTAAG AAGGTCACAA TAAAGCTGAA CTCCTTTTAA TGTGTAATGA      1440

AAGCAATTTG TAGGAAAGGC TCCATGGAAG ACATACATAT AGGCATCCTT CTTGATACTG      1500

AAAACAATCT TCTTGTTTGA AAGGAACTAT TGCTAAATGC AGAACAAGCT CATTGCAGTT      1560
```

5,766,888

39

40

-continued

| ACCTATTGTG | CATCTTTTTA | AATACTTGAT | TATGTAACCA | TAAATCTGAC | AGCATGTCTC | 1620 |
| ATTGGCTTAT | CTGGTAGCAA | ATCTAGGCCC | CGTCAGCCAC | CCTATTGACA | TTGGTGGCTC | 1680 |
| TGCTAAACCT | CAGGGGGACA | TGAAATCACT | GCCTCTTGGG | CATCTGGGGA | CACATGGTAA | 1740 |
| TGCTGTGCCT | TGACAGAAGT | ATTTGTTTAA | AGAAATGTCA | ATGCTGTCAT | TTGTGAACTC | 1800 |
| TATCAAAATT | AAAAATGTAT | TTTATCTACC | CTT | | | 1833 |

( 2 ) INFORMATION FOR SEQ ID NO:37:

( i ) SEQUENCE CHARACTERISTICS:
        ( A ) LENGTH: 461 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

| GGGGCTCTGG | CTGGACGCCG | CCGCCGCCGC | TGCCACCGCC | TCTGATCCAA | GCCACCTCCC | 60 |
| GCCAGAGAGG | TGTCATGGGC | TTCCAAAAGT | TCTCCCCCTT | CCTGGCTCTC | AGCATCTTGG | 120 |
| TCCTGTTGCA | GGCAGGCAGC | CTCCATGCAG | CACCATTCAG | GTCTGCCCTG | GAGAGCAGCC | 180 |
| CAGCAGACCC | GGCCACGCTC | AGTGAGGACG | AAGCGCGCCT | CCTGCTGGCT | GCACTGGTGC | 240 |
| AGGACTATGT | GCAGATGAAG | GCCAGTGAGC | TGGAGCAGGA | GCAAGAGAGA | GAGGGCTCCA | 300 |
| GAATCATTGC | CCAGAAGAGA | GCCTGTGACA | CTGCCACCTG | TGTGACTCAT | CGGCTGGCAG | 360 |
| GCTTGCTGAG | CAGATCAGGG | GGTGTGGTGA | AGAACAACTT | TGTGCCCACC | AATGTGGGTT | 420 |
| CCAAAGCCTT | TGGCAGGCGC | CGCAGGGACC | TTCAAGCCTG | A | | 461 |

( 2 ) INFORMATION FOR SEQ ID NO:38:

( i ) SEQUENCE CHARACTERISTICS:
        ( A ) LENGTH: 1864 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

| CCGGCCGCCA | GUCCAGCCGC | CCCUCGCCCG | GUGCCUAGGU | GCCCGGCCCC | ACACCGCCAG | 60 |
| CUGCUCGGCG | CCCGGGUCCG | CCAUGCGCUC | CGCCGCUGUC | CUGGCUCUUC | UGCUCUGCGC | 120 |
| CGGGCAAGUC | ACUGCGCUCC | CUGUGAACAG | CCCUAUGAAU | AAAGGGGAUA | CCGAGGUGAU | 180 |
| GAAAUGCAUC | GUUGAGGUCA | UCUCCGACAC | ACUUUCCAAG | CCCAGCCCCA | UGCCUGUCAG | 240 |
| CCAGGAAUGU | UUUGAGACAC | UCCGAGGAGA | UGAACGGAUC | CUUCCAUUC | UGAGACAUCA | 300 |
| GAAUUUACUG | AAGGAGCUCC | AAGACCUCGC | UCUCCAAGGC | GCCAAGGAGA | GGGCAACUCA | 360 |
| GCAGAAGAAA | CACAGCGGUU | UUGAAGAUGA | ACUCUCAGAG | GUUCUUGAGA | ACCAGAGCAG | 420 |
| CCAGGCCGAG | CUGAAAGAGG | CGGUGGAAGA | GCCAUCAUCC | AAGGAUGUUA | UGGAGAAAAG | 480 |
| AGAGGAUUCC | AAGGAGGCAG | AGAAAAGUGG | UGAAGCCACA | GACGGAGCCA | GGCCCCAGGC | 540 |
| CGUCCGGAG | CCCAUGCAGG | AGUCCAAGGC | UGAGGGGAAC | AAUCAGCCC | CUGGGGAGGA | 600 |
| AGAGGAGGAG | GAGGAGGAGG | CCACCAACAC | CCACCCUCCA | GCCAGCCUCC | CCAGCCAGAA | 660 |
| AUACCCAGGC | CCACAGGCCG | AGGGGACAG | UGAGGGCCUC | UCUCAGGGUC | UGGUGGACAG | 720 |
| AGAGAAGGGC | CUGAGUGCAG | AGCCAGGGUG | GCAGGCAAAG | AGAGAAGAGG | AGGAGGAGGA | 780 |
| GGAGGAGGAG | GCUGAGGCUG | GAGAGGAGGC | UGUCCCCGAG | GAAGAAGGCC | CCACUGUAGU | 840 |

| | | | | | | |
|---|---|---|---|---|---|---|
| GCUGAACCCC | CACCCGAGCC | UUGGCUACAA | GGAGAUCCGG | AAAGGCGAGA | GUCGGUCGGA | 900 |
| GGCUCUGGCU | GUGGAUGGAG | CUGGGAAGCC | UGGGGCUGAG | GAGGCUCAGG | ACCCCGAAGG | 960 |
| GAAGGGAGAA | CAGGAGCACU | CCCAGCAGAA | AGAGGAGGAG | GAGGAGUAGG | CAGUGGUCCC | 1020 |
| GCAAGGCCUC | UUCCGGGGUG | GGAAGAGCGG | AGAGCUGGAG | CAGGAGGAGG | AGCGGCUCUC | 1080 |
| CAAGGAGUGG | GAGGACUCCA | AACGCUGGAG | CAAGAUGGAC | CAGCUGGCCA | AGGAGCUGAC | 1140 |
| GGCUGAGAAG | CGGCUGGAGG | GGCAGCAGGA | GGAGGAGGAC | AACCGGGACA | GUUCCAUGAA | 1200 |
| GCUCUCCUUC | CGGGCCCGGG | CCUACGGCUU | CAGGGGCCCU | GGGCCGCAGC | UGCGACGAGG | 1260 |
| CUGGAGGCCA | UCCUCCCGGG | AGGACAGCCU | UGAGGCGGGC | CUGCCCCUCC | AGGUCCGAGG | 1320 |
| CUACCCCGAG | GAGAAGAAAG | AGGAGGAGGG | CAGCGCAAAC | CGCAGACCAG | AGGACCAGGA | 1380 |
| GCUGGAGAGC | CUGUCGGCCA | UUGAAGCAGA | GCUGGAGAAA | GUGGCCCACC | AGCUGCAGGC | 1440 |
| ACUACGGCGG | GGCUGAGACA | CCGGCUGGCA | GGGCUGGCCC | CAGGGCACCC | UGUGGCCCUG | 1500 |
| GCUCUGCUGU | CCCCUUGGCA | GGUCCUGGCC | AGAUGGCCCG | GACGCUGCUU | CCGGUAGGGA | 1560 |
| GGCAGCCUCC | AGCCUGCCCA | AGCCCAGGCC | ACCCUAUCGC | CCCCUACGCG | CCUUGUCUCC | 1620 |
| UACUCCUGAC | UCCUACCUGC | CCUGGAACAU | CCUUUGCAGG | GCAGCCCCAC | AACUUUAAAC | 1680 |
| AUUGACGAUU | CCUUCUCUGA | ACACAGGCAG | CUUUCUAGAA | GUUUCCCUUC | CUCCAUCCUA | 1740 |
| UCCACUGGGC | ACAACUGCAA | UAACUUCUGA | CCUUUUGGUG | AAAGCUGAGA | ACUCCUGACU | 1800 |
| GUAACAUAUU | CUGUAUGAAC | UUUAUCUAAA | GAAAAUAAA | UCUGUUCUGG | GCUCUUUCCU | 1860 |
| CUGA | | | | | | 1864 |

( 2 ) INFORMATION FOR SEQ ID NO:39:

( i ) SEQUENCE CHARACTERISTICS:
        ( A ) LENGTH: 592 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

| | | | | | | |
|---|---|---|---|---|---|---|
| GGTCGACTAC | CTGTGTGCAC | AGGATGCCTG | ACACCATGCT | GCCCGCCTGC | TTCCTCGGCC | 60 |
| TACTGGCCTT | CTCCTCCGCG | TGCTACTTCC | AGAACTGCCC | GAGGGCGGC | AAGAGGGCCA | 120 |
| TGTCCGACCT | GGAGCTGAGA | CAGTGCCTCC | CCTGCGGCCC | CGGGGGCAAA | GGCCGCTGCT | 180 |
| TCGGGCCCAG | CATCTGCTGC | GCGGACGAGC | TGGGCTGCTT | CGTGGGCACG | GCTGAGGCGC | 240 |
| TGCGCTGCCA | GGAGGAGAAC | TACCTGCCGT | CGCCCTGCCA | GTCCGGCCAG | AAGGCGTGCG | 300 |
| GGAGCGGGGG | CCGCTGCGCC | GCCTTCGGCG | TTTGCTGCAA | CGACGAGAGC | TGCGTGACCG | 360 |
| AGCCCGAGTG | CCGCGAGGTC | TTTCACCGCC | GCGCCCGCGC | CAGCGACCGG | AGCAACGCCA | 420 |
| CGCAGCTGGA | CGGGCCGGCC | GGGGCCTTGC | TGCTGCGGCT | GGTGCAGCTG | GCCGGGGCGC | 480 |
| CCGAGCCCTT | CGAGCCCGCC | CAGCCCGACG | CCTACTGAGT | CCCCGTGTTC | GTCCCACCGG | 540 |
| CGCGCTCTTC | GCGCCCGCCC | CTGCAGCACG | GACAATAAAC | CTCCGCCAAT | GC | 592 |

( 2 ) INFORMATION FOR SEQ ID NO:40:

( i ) SEQUENCE CHARACTERISTICS:
        ( A ) LENGTH: 176 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

| | | | | | |
|---|---|---|---|---|---|
| CTACCTGCCG | TCGCCCTGCC | AGTCCGGCCA | GAAGGCGTGC | GGGAGCGGGG | GCCGCTGCGC | 60
| GGTCTTGGGC | CTCTGCTGCA | GCCCGGACGG | CTGCCACGCC | GACCCTGCCT | GCGACGCGGA | 120
| AGCCACCTTC | TCCCAGCGCT | GAAACTTGAT | GGCTCCGAAC | ACCCTCGAAG | CGCGCC | 176

( 2 ) INFORMATION FOR SEQ ID NO:41:

( i ) SEQUENCE CHARACTERISTICS:
( A ) LENGTH: 2403 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:41:

| | | | | | |
|---|---|---|---|---|---|
| GCTCCTAACT | CCTGGCCAGA | AACAGCTCTC | CTCAACATGA | GAGCTGCACC | CCTCCTCCTG | 60
| GCCAGGGCAG | CAAGCTTAGC | CTTTGCTTCT | TGTTCTGCT | TTTTTGCTG | GCTAGACCGA | 120
| AGTGTACTAG | CCAAGGAGTT | GAAGTTTGTG | ACTTTGGTGT | TTCGGCATGG | ACACCGAAGT | 180
| CCCATTGACA | CCTTTCCCAC | TGACCCCATA | AAGGAATCCT | CATGGCCACA | AAGGATTTGG | 240
| CCAACTCACC | CAGCTGGCAT | GGAGCAGCAT | TATGAACTTG | GAGAGTATAT | AAGAAAGAGA | 300
| TATAGAAAAT | TCTTGAATGA | GTCCTATAAA | CATGAACAGG | TTTATATTCG | AAGCACAGAC | 360
| GTTGACCGGA | CTTTGATGAG | TGCTATGACA | AACCTGGCAG | CCCTGTTTCC | CCCAGAAGGT | 420
| GTCAGCATCT | GGAATCCTAT | CCTACTCTGG | GAGCCCATCC | CGGTGCACAC | AGTTCCTCTT | 480
| TCTGAAGATC | AGTTGCTATA | CCTGCGTTTC | AGGAACTGCC | CTCGTTTTCA | AGAACTTGAG | 540
| AGTGAGACTT | TGAAATCAGA | GGAATTCCAG | AAGAGGCTGC | ACCCTTATAA | GGATTTTATA | 600
| GCTACCTTGG | GAAAACTTTC | AGGATTACAT | GGCCAGGACC | TTTTTGGAAT | TTGGAGTAAA | 660
| GTCTACGACC | CTTTATATTG | TGAGAGTGTT | CACAATTTCA | CTTACCCTC | CTGGGCCACT | 720
| GAGGACACCA | TGACTAAGTT | GAGAGAATTG | TCAGAATTGT | CCCTCCTGTC | CCTCTATGGA | 780
| ATTCACAAGC | AGAAAGAGAA | ATCTAGGCTC | CAAGGGGGTG | TCCTGGTCAA | TGAAATCCTC | 840
| AATCACATGA | AGAGAGCAAC | TCAGATACCA | AGCTACAAAA | AACTCATCAT | GTATTCTGCG | 900
| CATGACACTA | CTGTGATGTG | CCTACAGATG | GCGCTAGATG | TTTACAACGG | ACTCCTTCCT | 960
| CCCTATGCTT | CTTGCCACTT | GACGGAATTG | TACTTTGAGA | AGGGGGAGTA | CTTTGTGGAG | 1020
| ATGTACTACC | GGAATGAGAC | GCAGCACGAG | CCGTATCCCC | TCATGCTACC | TGGATGCAGC | 1080
| CCCAGCTGTC | CTCTGGAGAG | GTTTGCTGAG | CTGGTTGGCC | CTGTGATCCC | TCAAGACTGG | 1140
| TCCACGGAGT | GTATGACCAC | AAACAGCCAT | CAAGGTACTG | AGAACAGTAC | AGATTAGTGT | 1200
| GCACAGAGAT | CTCTGTAGAA | GGAGTAGCTG | CCCTTCTCA | GGGCAGATGA | TGCTTTGAGA | 1260
| ACGTACTTTG | GCCATTACCC | CCCAGCTTTG | AGGAAAATGG | GCTTGGATG | ATTATTTAT | 1320
| GTTTTAGGGA | CCCCCAACCT | CAGGCAATTC | CTACCTCTTC | ACCTGACCCT | GCCCCACTT | 1380
| GCCATAAAAC | TTAGCTAAGT | TTTGTTTTGT | TTTTCAGCGT | TAATGTAAAG | GGGCAGCAGT | 1440
| GCCAAAATAT | AATCAGAGAT | AAAGCTTAGG | TCAAAGTTCA | TAGAGTTCCC | ATGAACTATA | 1500
| TGACTGGCCA | CACAGGATCT | TTTGTATTTA | AGGATTCTGA | GATTTTGCTT | GAGCAGGATT | 1560
| AGACAAGCCT | GTTCTTTAAA | TTGCTGAAAT | GGAACAGATT | TCAAAAAAAA | CGCCCACAAT | 1620
| CTAGGGTGGG | AACAAGGAAG | GAAAGATGTG | AATAGGCTGA | TGGGCAAAAA | ACCAATTTAC | 1680
| CCATCAGTTC | CAGCCTTCTC | TCAAGGAGAG | GCAAAGAAAG | GAGATACAGT | GGAGACATCT | 1740

| | | | | | | |
|---|---|---|---|---|---|---|
| GGAAAGTTTT | CTCCACTGGA | AAACTGCTAC | TATCTGTTTT | TATATTTCTG | TTAAAATATA | 1800 |
| TGAGGCTACA | GAACTAAAAA | TTAAAACCTC | TTGGTGTCCC | TTGGTCCTGG | AACATTTATG | 1860 |
| TTCCTTTTAA | AGAAACAAAA | ATCAAACTTT | ACAGAAAGAT | TTGATGTATG | TAATACATAT | 1920 |
| AGCAGCTCTT | GAAGTATATA | TATCATAGCA | AATAAGTCAT | CTGATGAGAA | CAAGCTATTT | 1980 |
| GGGCACAACA | CATCAGGAAA | GAGAGCACCA | CGTGATGGAG | TTTCTCCAGA | AGCTCCAGTG | 2040 |
| ATAAGAAGTG | TTGACTCTAA | AGTTGATTTA | AGGGCAGGCA | TGGTGGTTTA | CGCCTATAAT | 2100 |
| CCCAGCATTT | TGGGAGTCCG | AGGTGGGCAG | ATCACTTGAG | CTCAGGAGGT | CAAGATCAGC | 2160 |
| CTGGGCAACA | TGGTGAAACC | TTGGCTCTAC | ATAAAATACA | AAAACTTAGA | TGGGCATGGT | 2220 |
| GGTGTGTGCC | TATAGTCCAC | TACTTGTGGG | GCTAAGGCAG | GAGGATCACT | TGAGCCCCGG | 2280 |
| AGGTCGAGGC | TACAGTGAGC | CAAGAGTGCA | CTACTGTACT | CCAGCCAGGG | CAAGAGAGCG | 2340 |
| AGACCCTGTC | TCAATAAATA | AATAAATAAA | TAAATAAATA | AATAAATAAA | TAAAAAAAAA | 2400 |
| AAA | | | | | | 2403 |

( 2 ) INFORMATION FOR SEQ ID NO:42:

( i ) SEQUENCE CHARACTERISTICS:
        ( A ) LENGTH: 111 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

| | | | | | |
|---|---|---|---|---|---|
| ATGTGGGTCC | CGGTTGTCTT | CCTCACCCTG | TCCGTGACGT | GGATTGGTGC | TGCACCCCTC | 60 |
| ATCCTGTCTC | GGATTGTGGG | AGGCTGGGAG | TGCGAGAAGC | ATTCCCAACC | C | 111 |

DETECTION OF CARCINOMA METASTASES BY NUCLEIC ACID AMPLIFICATION

This application is a continuation of application Ser. No. 08/357,565, filed Dec. 16, 1994, issued as U.S. Pat. No. 5,543,296, which is a continuation of application Ser. No. 08/096,110, filed Jul. 22, 1993, now abandoned, which is a continuation of application Ser. No. 07/720,061, filed Jun. 26, 1991, now abandoned.

This invention arose under federal funding as provided for the terms of Grant No. 5K12AG0035304 awarded by the National Institutes of Health.

BACKGROUND OF THE INVENTION

1. Field of the Invention

The present invention relates to the fields of molecular biology and oncology and provides novel methods for the detection of carcinoma metastases by nucleic acid amplification. In a preferred embodiment, carcinoma metastases are identified in hematopoietic tissues by detection of normal non-hematopoietic RNA expressed by the metastatic carcinoma cells. Detection of non-hematopoietic RNA sequences indicates the presence of metastatic disease. The methods have applications in the diagnosis, staging, and monitoring of carcinoma patients.

2. Description of Related Art

Recent advances in cancer therapeutics have demonstrated the need for more sensitive staging and monitoring procedures to ensure initiation of appropriate treatment, to define the end points of therapy and to develop and evaluate novel treatment modalities and strategies. In the management of carcinoma patients, the choice of appropriate initial treatment depends on accurate assessment of the stage of the disease. Patients with limited or regional disease generally have a better prognosis and are treated differently than patients who have distant metastases (Minna et al., 1989, *Cancer Principals and Practices of Oncology*, DeVita et al. ed. Lippincott, Philadelphia pp. 591–705, which is incorporated herein by reference). However, conventional techniques to detect these metastases are not very sensitive.

For example, the prognosis and therapeutic management of both major histological subgroups of lung cancer (small cell and non-small cell) depend upon the stage of disease activity at the time of diagnosis (Green, 1989, *Lung Cancer* 5:178–185, which is incorporated herein by reference). Patients with non-small cell lung cancers (NSCLC) comprise approximately 75% of lung cancers. This histological subgroup of lung cancer has been considered relatively resistant to chemotherapy. However, NSCLC are often curable by surgical resection (and occasionally by radiation therapy) in patients with stages I, II, or IIIA disease who do not have occult distant metastases.

Unfortunately, conventional staging procedures to detect metastatic disease are not very sensitive. Approximately 25% to 30% of stage I NSCLC patients are not cured by primary tumor resection because they have metastases that are not identified by standard methods during preoperative staging. The development of more sensitive techniques to detect metastases could identify those NSCLC patients who will not be cured by local surgical tumor resection, who would benefit from the administration of effective systemic therapies. Similarly, more sensitive methods to detect metastases in other types of carcinomas would identify patients who will not be cured by local therapeutic measures, for whom effective systemic therapies would be more appropriate.

The inadequacy of current staging methods also adversely effects the management of the other major histological type of lung cancer, small cell lung carcinoma (SCLC). In contrast to NSCLC, SCLC is very sensitive to chemotherapy and radiation therapy but is generally believed to be incurable by surgery alone since these tumors have usually metastasized to distant sites at the time of diagnosis. Approximately 25% to 35% of limited disease patients who achieve complete remissions with therapy have durable remissions, and two years event-free survival, following treatment. Current staging procedures cannot distinguish those who will have earlier relapses despite achieving initial complete remission. Most SCLC patients who achieve complete remissions have minimal residual disease (MRD) which cannot be detected by conventional methods. More sensitive methods to detect metastases are needed for identifying limited disease patients at high risk for early tumor recurrence who may benefit from additional systemic therapy.

Immunocytological procedures have been used to detect cancer cells in peripheral blood and bone marrow specimens unsuspected on the basis of conventional morphological evaluations (Sobol et al., 1982, *Clin. Immunopathol.* 24:139–144, and Sobol et al., 1985, *Cancer* 56:2005–2010, incorporated herein by reference). Immunohistochemical and immunofluorescence techniques have been used to identify antigens expressed by carcinomas that are not expressed by hematopoietic tissues (Sobol et al., 1986, *Cancer Research* 46:4746–4750, and Sobol et al., 1987, *Ann. Intern. Med.* 105:698–700). Several investigators have employed monoclonal antibody immunocytology to detect bone marrow metastases in carcinoma patients not identified by standard morphological examinations (Cannon et al., 1988, *Eur. J. Cancer Clin. Oncol.* 24:147–150; Berendsen et al., 1988, *J. Clin. Pathol.* 41:273–276; and Stahel et al., 1985, *J. Clin. Oncol* 3:455–461). However, immunocytological and standard morphological evaluations can reliably detect only 1% to 5% malignant cells in a mixed population with normal hematopoietic cells (Wright et al., 1987, *J. Clin. Oncology* 5:735–741).

Nucleotide amplification techniques provide rapid and sensitive methods for detecting specific nucleotide sequences (Mullis et al., 1986, *Cold Spring Harbor Symposium Quant. Biol.* 5:263–273, and Saiki et al., 1988, *Science* 2:487–491, which are incorporated herein by reference). Cell mixing experiments have demonstrated that polymerase chain reaction (PCR) analysis can identify as few as $1:10^4$ or $1:10^5$ cells that contain a target gene sequence (Kawasaki et al., 1987, *Proc. Natl. Acad. Sci. U.S.A.* 85:5698–5702, and Crescenzi et al., 1988, *Proc. Natl. Acad. Sci. U.S.A.* 85:4869–4873, which are incorporated herein by reference).

PCR has been employed to detect minimal residual disease activity in patients with hematopoietic malignancies (Fey et al., 1991, *Eur. J. Cancer* 27:89–94, and PCT Patent Publication No. WO 89/08717). These methods rely on the identification of abnormal nucleotide sequences resulting from recurring chromosome translocations which characterize the hematological malignancy. Primers flanking the chromosome break points are employed to amplify the aberrant nucleotide sequences which result from the translocation event. In contrast, recurring chromosome translocations are not a common feature of carcinomas. Some carcinomas are characterized by aberrant oncogene or tumor suppressor gene nucleotide sequences (Cooper, 1990, *Oncogenes* Jones and Burnlett Publishers). However, these abnormal nucleotide sequences are either too diverse, poorly characterized, or infrequent to serve as targets for a practical, generally applied nucleic acid amplification procedure to detect metastatic carcinomas. Novel methods are needed to exploit the sensitivity of nucleic acid amplification procedures to detect metastatic carcinoma disease activity. The present invention meets these needs.

SUMMARY OF THE INVENTION

The invention provides a method for detecting carcinoma metastases in body tissues and fluids that comprise the steps of: (a) treating a sample containing nucleic acid from the cells of the body tissues and fluids under conditions for amplifying a target carcinoma associated sequence in an amplification reaction mixture that comprises a primer pair for specifically amplifying the target carcinoma associated sequence, to provide an amplified sequence if the target carcinoma associated sequence is present, wherein the target carcinoma associated sequence is indicative of carcinoma metastases in the body tissues and fluids; and (b) determining if amplification has occurred.

In another aspect, the invention provides oligonucleotide primers and probes for amplifying and detecting metastatic disease in body tissues and fluids, wherein the primers are suitable for amplifying a target carcinoma associated sequence, which sequence is preferentially expressed in carcinoma tumor cells and not in the body tissues and fluids to be analyzed for detecting carcinoma metastases.

In another aspect, the invention provides kits for detecting metastatic disease in body tissues and fluids, the kits comprising: (a) a primer pair for amplifying a target carcinoma associated sequence, which sequence is preferentially expressed in carcinoma cells and not in resident cells normally present in the body tissues and fluids.

In another aspect, the invention provides a method for identifying a carcinoma associated RNA sequence suitable as a cancer marker for detecting carcinoma metastases in body tissues or fluids comprising the steps of: (a) isolating negative control mRNA from non-carcinoma cells; (b) isolating positive control mRNA from carcinoma cells; (c) reverse transcribing and amplifying the negative and positive control mRNAs in separate amplification reaction mixtures comprising a primer pair for specifically amplifying a candidate carcinoma associated sequence, wherein the sequence is normally expressed by epithelial cells but not by the non-carcinoma cells; and (d) detemining if amplification has occurred in the positive control sample and if amplification has failed in the negative control sample.

DETAILED DESCRIPTION

The present invention provides a method for detecting carcinoma associated nucleic acids in body tissues and fluids. In the preferred embodiment of the invention, the nucleic acids to be detected are carcinoma associated RNAs.

The invention is useful for detecting and monitoring carcinoma patients. In another aspect, the detection of carcinoma metastases has applicability in assessing the suitability of remission bone marrow specimens for carcinoma therapies incorporating autologous bone marrow transplantation. The availability of the present methods for detecting metastatic disease has utility in redefining the staging criteria for carcinomas and aide in determining the most appropriate type of initial therapy. The improved methods to detect metastases permit more precise documentation of complete remissions and early relapses. This information provides useful guidance for making decisions as to whether therapy should be continued, reinstituted or ceased and potentially results in more appropriate overall therapy for carcinoma patients. These novel methods provide means towards more effective management of carcinomas.

According to the present methods, RNA is extracted from cells in body tissues or fluids, for example, hematopoietic tissue such as bone marrow or peripheral blood and incubated with reverse transcriptase and deoxyribonucleoside triphosphates to generate cDNA. Subsequently, amplification procedures are employed to detect gene sequences expressed by carcinoma cells but not by the resident non-carcinoma cells normally present in the sample body tissue or fluid. In a preferred embodiment, PCR analysis of carcinoma associated mRNA is used to detect carcinoma cells in bone marrow specimens. Following reverse transcription, DNA polymerase and the up-stream and down-stream primers for the target sequences of interest are added to the reaction mixture to amplify the target gene sequence. In one embodiment, following 20–40 cycles of amplification using PCR methods, the reaction mixture is extracted with chloroform and the aqueous phase is electrophoresed in an agarose gel. The gel is stained with ethidium bromide and photographed to determine the presence of the target sequence. Oligonucleotide probes may be used to unequivocally identify the target sequence using Southern or dot blot methodologies.

In contrast to prior methods for cancer detection, the target nucleic acid is not necessarily an oncogene mRNA product. Carcinomas are non-hematopoietic cancers and no common recurrent translocations or uniform gene aberrations have been identified for reproducibly identifying metastasized carcinomas by nucleic acid amplification methods. Conventional methods are useful for detecting metastases where 1–5% of the cells analyzed display the cytological characteristics of cancer cells.

The present invention for detecting carcinoma metastases also provides methods for identifying carcinoma associated nucleic acid sequences useful as cancer markers. As used herein, the term "carcinoma" refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas.

As used herein, the term "carcinoma associated sequences" or "carcinoma associated RNA sequences" refers to nucleic acid sequences expressed by carcinoma cells, that are not expressed by the resident cells normally present in the sample body tissues and fluids. As used herein, generally, carcinoma associated sequences are RNAs.

The present invention provides methods for identifying particular target nucleic acids and amplifying those nucleic acids, for detecting carcinoma metastases in body tissues or fluids such as hematopoietic tissues (bone marrow, peripheral blood, and lymph nodes), and pleural effusions. The target nucleic acids, as described herein, are carcinoma associated RNA transcripts produced in cancer cells, as well as in healthy cells from which the tumors arise. However, according to the invention, the presence of metastatic disease is determined by amplifying and detecting these target nucleic acids in cells of tissues or fluids which do not normally express the target genes. In the preferred embodiment of the invention, the target genes are not normally expressed in hematopoietic cells.

To determine whether or not a particular carcinoma has metastasized, the specific type of carcinoma can be considered for determining suitable target nucleic acids to be detected. For example, genes expressed by carcinomas, that are suitable for detecting metastases in bone marrow and peripheral blood specimens, would include genes encoding epithelial antigens or neuroendocrine antigens that are not expressed by hematopoietic cells. Some target nucleic acids, particularly those encoding epithelial antigens, such as the antigen recognized by the monoclonal antibody KS¼ (Bumol et al., 1988, *Hybridoma* 7(4): 407–415), are useful for detecting a broad spectrum of metastasized carcinomas.

Criteria for selecting target genes for analysis include gene expression by a large percentage of carcinoma cells and the absence of expression by hematopoietic elements. Target genes include but are not limited to chromogranin A (chromo A), neuron specific enolase, calcitonin, bombesin, neural cell adhesion molecules (NCAM), synaptophysin (synapto), L-dopa decarboxylase, neurophysin I and II (neuro I, neuro II), parathyroid related hormone of malignancy, selected SCLC antigens defined by monoclonal antibodies, and the pan-carcinoma antigens recognized by the monoclonal antibody KS¼. It will be obvious to one of ordinary skill in the art that the suitability of any particular target gene for use in the present methods depends on the particular primers, samples, and conditions employed. Methods for assessing the suitability of a target gene as a cancer marker are disclosed herein and demonstrated in the examples.

The sensitivity of the present methods distinguish the invention from prior methods for detecting metastasized tumor cells. Previous methods include histological and serum chemistry analyses, physical examinations, bone scans, and X-rays. The examples disclosed herein demonstrate PCR amplification for detecting target gene products. However, any of a number of amplification methods are equally suitable for practicing the invention.

The term "amplification reaction system" refers to any in vitro means for multiplying the copies of a target sequence of nucleic acid. Such methods include but are not limited to polymerase (PCR), DNA ligase, (LCR), Qβ RNA replicase, and RNA transcription-based (TAS and 3SR) amplification systems.

The term "amplifying" which typically refers to an "exponential" increase in target nucleic acid is being used herein to describe both linear and exponential increases in the numbers of a select target sequence of nucleic acid.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Depending upon the context, the mixture can be either a complete or incomplete amplification reaction mixture.

The systems described below are practiced routinely by those of skill in the relevant art. They have been described in detail by others and are summarized below. This invention is not limited to any particular amplification system. As other systems are developed, those systems may benefit by practice of this invention. A recent survey of amplification systems was published in *Bio/Technology* 8:290–293, April 1990, incorporated herein by reference. The following four systems are described below for the convenience of those not familiar with amplification systems and to provide an understanding of the breadth of the present invention.

Amplification of DNA by PCR is disclosed in U.S. Pat. Nos. 4,683,195 and 4,683,202 (both of which are incorporated herein by reference). Methods for amplifying and detecting nucleic acids by PCR using a thermostable enzyme are disclosed in U.S. Pat. No. 4,965,188, which is incorporated herein by reference.

PCR amplification of DNA involves repeated cycles of heat-denaturing the DNA, annealing two oligonucleotide primers to sequences that flank the DNA segment to be amplified, and extending the annealed primers with DNA polymerase. The primers hybridize to opposite strands of the target sequence and are oriented so that DNA synthesis by the polymerase proceeds across the region between the primers, effectively doubling the amount of the DNA segment. Moreover, because the extension products are also complementary to and capable of binding primers, each successive cycle essentially doubles the amount of DNA synthesized in the previous cycle. This results in the exponential accumulation of the specific target fragment, at a rate of approximately 2-fold per cycle, where n is the number of cycles.

In the disclosed embodiment, Taq DNA polymerase is preferred although this is not an essential aspect of the invention. Taq polymerase, a thermostable polymerase, is active at high temperatures. Methods for the preparation of Taq are disclosed in U.S. Pat. No. 4,889,818 and incorporated herein by reference. Taq polymerase is available from Perkin Elmer Cetus Instruments (PECI). However, other thermostable DNA polymerases isolated from other Thermus species or non Thermus species (e.g., *Thermus thermophilus* or *Thermotoga maritima*), as well as non-thermostable DNA polymerase such as T4 DNA polymerase, T7 DNA polymerase, *E. coli* DNA polymerase I, or the Klenow fragment of *E. coli*, can also be used in PCR. Methods for providing thermostable DNA polymerases are provided in copending Ser. No. 08/148,133, which is a continuation of Ser. No. 455,967, filed Dec. 22, 1989, now abandoned; U.S. Pat. No. 5,374,553; U.S. Pat. No. 5,405,774; and U.S. Pat. No. 5,455,170; and Ser. No. 590,490, filed Sep. 28, 1990, now abandoned, which are all incorporated herein by reference.

The nucleoside-5'-triphosphates utilized in the extension process, typically dATP, dCTP, dGTP, and dTTP, are present in total concentration typically ranging from 0.05 mM to 0.5 mM during the extension reaction, although preferably the concentration is between 0.1 mM and 0.2 mM.

As used herein, the term "primer" refers to an oligonucleotide capable of acting as a point of initiation of DNA synthesis when annealed to a nucleic acid template under conditions in which synthesis of a primer extension product is initiated, i.e., in the presence of four different nucleotide triphosphates and a DNA polymerase in an appropriate buffer ("buffer" includes pH, ionic strength, cofactors, etc.) and at a suitable temperature.

The choice of primers for use in PCR determines the specificity of the amplification reaction. Primers used in the present invention are oligonucleotides, usually deoxyribonucleotides several nucleotides in length, that can be extended in a template-specific manner by the polymerase chain reaction. The primer is sufficiently long to prime the synthesis of extension products in the presence of the agent for polymerization and typically contains 10–30 nucleotides, although that exact number is not critical to the successful application of the method. Short primer molecules generally require cooler temperatures to form sufficienfly stable hybrid complexes with the template.

Synthetic oligonucleotides can be prepared using the triester method of Matteucci et al.,1981, *J. Am. chem. Soc.* 103:3185–3191. Alternatively automated synthesis may be preferred, for example, on a Biosearch 8700 DNA Synthesizer using cyanoethyl phosphoramidite chemistry.

For primer extension to occur, this primer must anneal to the nucleic acid template. Not every nucleotide of the primer must anneal to the template for extension to occur. The primer sequence need not reflect the exact sequence of template. For example, a non-complementary nucleotide fragment may be attached to the 5' end of the primer with the remainder of the primer sequence being complementary to the template. Alteratively, non-complementary bases can be interspersed into the primer, provided that the primer sequence has sufficient complementarily with the template for annealing to occur and allow synthesis of a complementary DNA strand.

Due to the enormous amplification possible with the PCR process, small levels of DNA carryover from samples with high DNA levels, positive control templates or from previous amplifications can result in PCR product, even in the absence of added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, *Nature*, 339:237–238 and Kwok, and Orrego, in: Innis et al. eds., 1990 *PCR Protocols: A Guide to Methods and Applications*, Academic Press, Inc., San Diego, Calif., which are incorporated herein by reference.

One particular method for minimizing the effects of cross contamination of nucleic acid amplification is described in U.S. Ser. No. 609,157, filed Nov. 2, 1990, now abandoned, which is incorporated herein by reference. The method involves the introduction of unconventional nucleotide bases, such as dUTP, into the amplified product and exposing carryover product to enzymatic and/or physical-chemical treatment to render the product DNA incapable of serving as a template for subsequent amplifications. For example, uracil-DNA glycosylase will remove uracil residues from PCR product containing that base. The enzyme treatment results in degradation of the contaminating carryover PCR product and serves to "sterilize" the amplification reaction.

Amplification systems such as PCR require a target nucleic acid in a buffer compatible with the enzymes used to amplify the target The target nucleic acid can be isolated from a variety of biological materials including tissues, body fluids, feces, sputum, saliva, and the like. In the preferred embodiment of the invention, the target nucleic acid is a carcinoma associated RNA sequence and the sample to be tested for the presence of the target nucleic acid is contained in a hematopoietic tissue sample, for example, bone marrow aspirate biopsies, peripheral blood, lymph node cell biopsies or aspirates. Other samples suitable for analysis include but are not limited to pleural fluid, ascites, and cerebrospinal fluid.

To amplify a target nucleic acid sequence in a sample, the sequence must be accessible to the components of the amplification system. In general, this accessibility is ensured by isolating the nucleic acids from a crude biological sample. A variety of techniques for extracting nucleic acids from biological samples are known in the art. For example, see those described in Sambrook et al., *Molecular Cloning: A Laboratory Manual* (New York, Cold Spring Harbor Laboratory, 1989); Arrand, Preparation of Nucleic Acid Probes, in pp. 18–30, *Nucleic Acid Hybridization: A Practical Approach* (Ed Hames and Higgins, IRL Press, 1985); or, in *PCR Protocols*, Chapters 18–20 (Innis et al., ed., Academic Press, 1990), which are all incorporated herein by reference.

In general, the nucleic acid in the sample will be a sequence of RNA or DNA. RNA is prepared by any number of methods; the choice may depend on the source of the sample and availability. Methods for preparing RNA are described in Davis et al, 1986, *Basic Methods in Molecular Biology*, Elsevier, N.Y., Chapter 11; Ausubel et al., 1987, *Current Protocols in Molecular Biology*, Chapter 4, John Wiley and Sons, NY; Kawasaki and Wang, 1989, *PCR Technology*, ed. Erlich, Stockton Press NY; Kawasaki, 1990, *PCR Protocols: A Guide to Methods and Aplications*, Innis et al. eds. Academic Press, San Diego; and Wang and Mark, 1990, *PCR Protocols: A Guide to Methods and Applications*, Innis et al. eds. Academic Press, San Diego; all of which are incorporated herein by reference. Chomczynski and Sacchi, 1987, *Anal. Biochem* 162:156–159, which is incorporated herein by reference, provides a single-step method of RNA isolation by acid guanidinium thiocyanate-phenol-chloroform extraction. Those of skill in the art will recognize that whatever the nature of the nucleic acid, the nucleic acid can be amplified merely by making appropriate and well recognized modifications to the method being used.

It is preferred, but not essential that the thermostable DNA polymerase is added to the reaction mix after both the primer and the template are added. Alternatively, for example, the enzyme and primer are added last, or the $MgCl_2$, or template plus $MgCl_2$ are added last. It is generally desirable that at least one component, that is essential for polymerization, not be present, until such time as the primer and template are both present and the enzyme can bind to and extend the desired primer/template substrate. This modification of PCR is referred to as "hot start" and is described in U.S. Pat. No. 5,411,876, which is incorporated herein by reference.

Those skilled in the art will know that the PCR process is most usually carried out as an automated process with a thermostable enzyme. In this process, the reaction mixture is cycled through a denaturing temperature range, a primer annealing temperature range, and an extension temperature range. Generally, the annealing and extension temperature ranges overlap, and consequently, PCR is often practiced as a two-step cycling reaction comprising a denaturing step and an annealing/extension step. A machine specifically adapted for use with a thermostable enzyme is disclosed more completely in EP No. 236,069, which is incorporated herein by reference, and is commercially available from PECI.

The ligase chain reaction is described in PCr Patent Publication No. WO 89/09835, which is incorporated herein by reference. The process involves the use of ligase to join oligonucleotide segments that anneal to the target nucleic acid. Ligase chain reaction (LCR) results in amplification of an original target molecule and can provide millions of copies of product DNA. Consequently, the LCR results in a net increase in double-stranded DNA. The present detection methods are applicable to LCR, as well as PCR. LCR requires an oligonucleotide probe for detecting the product DNA.

Another amplification scheme exploits the use of the replicase from the RNA bacteriophage Qβ. In this amplification scheme, a modified recombinant bacteriophage genome with a sequence specific for the targeted sequence is initially hybridized with the nucleic acid to be tested. Following enrichment of the duplexes formed between the bacteriophage probe and the nucleic acid in a sample, Qβ replicase is added, which, upon recognizing the retained recombinant genome, begins making large numbers of copies.

The Qβ system does not require primer sequences and there is no heat denaturation step as with the PCR and LCR amplification systems. The reaction occurs at one temperature, typically 37° C. The preferred template is a substrate for the Qβ replicase, midvariant-1 RNA. A very large increase in the templates is achieved through the use of this system. A review of this amplification system can be found in the International Patent Application Pub. No. WO 87/06270 and in Lizardi et al., 1988, *Bio/Technology* 6:1197–1202.

The 3SR system is a variation of an in vitro transcription based amplification system. A transcription-based amplification system (TAS) involves the use of primers that encode a promoter to generate DNA copies of a target strand and the production of RNA copies from the DNA copies with an RNA polymerase. See, e.g., Example 9B of U.S. Pat. No. 4,683,202 and EP No. 310,229. The 3SR System is a system which uses three enzymes to carry out an isothermal replication of target nucleic acids.

The system begins with a target of single-stranded RNA to which a T7 RNA DNA primer is bound. By extension of the primer with reverse transcriptase, a cDNA is formed, and RNAseH treatment frees the cDNA from the heteroduplex. A second primer is bound to the cDNA and a double stranded cDNA is formed by DNA polymerase (i.e., reverse transcriptase) treatment. One (or both) of the primers encodes a promoter, i.e., the promoter for T7 RNA polymerase, so that the double-stranded cDNA is transcription template for T7 RNA polymerase.

Transcription competent cDNAs yield antisense RNA copies of the original target. The transcripts are then converted by the reverse transcriptase to double standard cDNA containing double-stranded promoters, optionally on both ends in an inverted repeat orientation. These DNAs can yield RNAs, which can reenter the cycle. A more complete description of the 3SR system can be found in Guatelli et al., 1990, *Proc. Natl. Acad. Sci. U.S.A.* 87:1874–1878, and EP No. 329,822, both of which are incorporated herein by reference. The TAS system is also described in Gingeras et al. in Innis et al. eds., 1990, *PCR Protocols*, Academic Press, San Diego, which is incorporated herein by reference.

In the process described herein, a sample is provided which contains, or is suspected of containing, a particular oligonucleotide sequence of interest, the "target nucleic acid." The target may be RNA or DNA or an RNA/DNA hybrid. The target may be single stranded or double stranded. According to the present invention, the target nucleic acid is a carcinoma associated sequence. For example, in one aspect of the invention, a carcinoma may be attributable to an integrated virus, such as human papilloma virus (HPV), and cervical cancer cells would contain HPV DNA sequences. Detection of HPV DNA sequences in non-cervical cells, such as bone marrow, by the present methods provides, evidence of metastatic disease. Target preparation will be carried out in a manner appropriate for the particular amplification process to be implemented. For example, in a PCR method where the target nucleic acid is single-stranded, such as mRNA, the target may be first reverse-transcribed into cDNA, prior to amplification.

Although the PCR procedure described above assumed a double-stranded target, this is not a necessity. After the first amplification cycle of a single-stranded DNA target, the reaction mixture contains a double-stranded DNA molecule consisting of the single-stranded target and a newly synthesized complementary strand. Similarly, following the first amplification cycle of an RNA/cDNA target, the reaction mixture contains a double-stranded cDNA molecule and a duplicate of the original RNA/cDNA target. At this point, successive cycles of amplification proceed as described above. In the present methods, the target of amplification is a single-stranded RNA, and the first amplification cycle is the reverse transcription step.

Methods for reverse transcribing RNA into cDNA are well known and described in Sambrook et al., supra. Alteratively, preferred methods for reverse transcription utilize thermostable DNA polymerases. These methods are described in U.S. Pat. No. 5,322,770, and WO 90/07641 filed Dec. 21, 1990, incorporated herein by reference. U.S. Pat. No. 5,322,770 describes a procedure for coupled reverse transcription/amplification of an RNA template using a thermostable DNA polymerase.

Target genes are selected from those that are preferentially expressed in epithelial tissues and not in hematopoietic tissues. Amplification primers are preferably designed to hybridize to exons whose sequences are adjacent in mRNA. In this manner, background amplification of genomic sequences is minimized and readily distinguished from target amplification by size.

According to the invention, for selecting target genes suitable as cancer markers, primers are tested using available characterized carcinoma cell lines as positive controls, for example, from the American Type Culture Collection, Rockville, Md., and representative body tissues and fluid specimens, for example, bone marrow aspirates, from individuals without carcinomas, as negative controls in amplification reactions. For example, the existence of pseudogenes is determined so that a false positive result will not be obtained if genomic DNA contaminates a target sample. When a genomic pseudogene is present methods for avoiding pseudogene amplification will be obvious to one of ordinary skill in the art by, for example, selecting a different target sequence region to be amplified or altering the specificity of the reaction by varying primer length or cycling parameters.

Although the target carcinoma associated RNA sequences are preferentially expressed in epithelial tissues, the body fluids or tissues to be evaluated may express target sequences at a low basal level. Because of the sensitivity of the PCR method, even basal level expression can compromise a test (Chelly et al., 1988, *Nature* 330:858–860). Consequently, the identification of carcinoma associated sequences for detecting carcinoma metastases in the selected body tissues and fluids preferably includes screening amplification and detection evaluations to ascertain (1) the absence of (failure to amplify and detect) the target carcinoma associated sequence and non-malignant cells from representative samples of body tissues and fluids to be tested for carcinoma metastases and (2) the presence of (ability to amplify and detect) the target carcinoma associated sequences and representative carcinoma cells. Accordingly, it is preferred that normal bone marrow specimens and specimens from patients with hematopoietic cancers, as well as normal peripheral blood samples are analyzed to determine preferred primers and targets for detecting metastasized carcinomas. If necessary, one of skill in the art can readily modify the amplification and/or detection methods to distinguish between a low basal level of expression in a non-carcinoma cell, and a positive amplification from a carcinoma cell sample. For example, the amount of sample, cycling parameters, and detection scheme are modified as needed to reduce the likelihood of a false positive.

Body tissues and fluids suitable for detecting carcinoma metastases include, but are not limited to, those which are currently evaluated to detect metastatic dissects by standard, less sensitive cytological methods: bone marrow aspirates and biopsies, pleural effusions, ascites, cerebrospinal fluid, lymph node aspirates and biopsies, and peripheral blood.

Candidate carcinoma associated sequences include but are not limited to RNA sequences which encode proteins previously shown by conventional protein detection assays to be preferentially expressed by carcinoma cells and not by cells in the body tissues and fluids that will be evaluated for carcinoma metastases. Target sequences for the detection of metastasized carcinomas are briefly described below. For any particular target sequence, it will be obvious to one of ordinary skill in the art to select primers for amplification in accordance with the description of the methods provided herein.

KS¼ pan-carcinoma antigen is a monoclonal antibody defined antigen expressed by most carcinomas, including small cell and non-small cell lung cancers (Perez and Walker, 1990, J. Immunol. 142:3662-3667, and Bumal, 1988, Hybridoma 7(4):407-415, which are incorporated herein by reference). A cDNA sequence corresponding to KS¼ mRNA is provided in the sequence listing as SEQ ID NO: 32. The frequency of expression in SCLC or KS¼ is approximately 80%. This gene is also highly expressed in other carcinomas.

Synaptophysin and bombesin/gastrin releasing peptide (GRP) are both neuroendocrine peptides and both are frequently expressed by small cell carcinomas (approximately 60%-80%) Kayser et al., 1988, Pathology Research and Practice 183(4):412-417; and Spindel et al., 1986, Proc. Natl. Acad. Sci. U.S.A. 83:19-23, which are incorporated herein by reference). cDNA sequences, corresponding to two species of GRP mRNA, are provided in the sequence listing as SEQ ID NO: 33 and SEQ ID NO: 34. L-dopa decarboxylase is also expressed by a high percentage of small cell lung carcinoma cells (approximately 80%) (Gazdar et al., 1988, Cancer Research 48:4078-4082, which is incorporated herein by reference).

Neuron specific enolase is expressed by a high percentage of small lung cell carcinomas (60%-80%) (Kayser et al., 1988, Pathology Research Practice 143:412-417, which is incorporated herein by reference). Preferably, for practicing the present invention, primers for this gene should avoid sequence homologies with other forms of enolases that are frequently expressed by non-neuroendocrine tissues.

Parathyroid related hormone (PRH) may be expressed by more than 50% of small lung cell carcinomas, as well as in several other carcinomas. PRH is also expressed by hematopoietic malignancies associated with HTLV I infection. In a preferred embodiment of the invention, primers that correspond to amino acids 35 to 139 are selected to avoid regions of homology with parathyroid hormone and include all known forms of PRH (Suva, 1989, Gene 77(1):95-105; and Martin et al., 1989, Recent Progress in Hormone Research 45:467-506). A cDNA sequence corresponding to PRH mRNA is provided in the sequence listing as SEQ ID NO: 35.

Calcitonin may be more variably expressed by small cell lung carcinomas (Ed brooke et al. EMBO J. 4:715-724 Jonas et al., 1985, Proc. Natl. Acad. Sci. U.S.A. 82:1994-1998, and Russell et al., 1990, Mol Cell Endocrin. 71(1):1-12, which are incorporated herein by reference). cDNA sequences corresponding to calcitonin and calcitonin gene related peptide mRNA's are provided in the sequence listing as SEQ ID NO: 36 and SEQ ID NO: 37. Calcitonin and/or the calcitonin gene related peptide (CGRP) are expressed by 40%-60% of small cell lung carcinomas. In the disclosed example, primers are designed as consensus primers for amplifying both calcitonin and CGRP sequences to enhance the yield of cancers detected.

Chromogranin A is associated with secretory granules found in normal neuroendocrine cells and in neuroendocrine tumors (Konecki et al., 1987, JBC 262:17026-17030, and Sobol et al., 1986, Annals of Internal Medicine 105(5):698-700, which are incorporated herein by reference). The chromogranin A mRNA sequence is provided in the specification as SEQ ID NO: 38. The protein is expressed by 40%-60% of small lung cell carcinomas. According to the preferred embodiment, primers are selected from the middle region of the molecule. The amino and carboxy terminal regions share homology with chromogranin B and C which may have less specificity for neuroendocrine cells.

Neurophysins are precursors of oxytocin and vasopressin which are expressed by approximately 30%-50% of small cell carcinomas (Mohr et al., 1985, FEBS Letters 193:12-16; North et al., 1988, Cancer 62(7):1343-1347, and Kibbelaar et al., 1989, J. Pathology 159:23-28, which are incorporated herein by reference). cDNA sequences corresponding to mRNA's encoding vasopressin and oxytocin precursors are provided in the specification as SEQ ID NO: 39 and SEQ ID NO: 40). Consensus primers to amplify both neurophysins I and II may be utilized to enhance the yield of small cell lung carcinomas detected.

Other candidate target sequences include but are not limited to ovarian carcinoma antigen (CA125) (Yu et al., 1991, Cancer Res. 51(2):468-475); prostatic acid phosphate (Tailor et al., 1990, Nuc. Acids Res 18(16):4928 see SEQ ID NO: 41); prostate specific antigen (Henttu and Vihko, 1989, Biochemical and Biophys Res. Comm 160(2):903-910 see SEQ ID NO: 42); melanoma-associated antigen p97 (Estin et al., 1989, J. Nat. Cancer. Instit. 81(6):445-446); melanoma antigen gp75 (Vijayasardahi et al., 1990, J. Experimental Medicine 171(4):1375-1380 see EMBL Accession number 851455 and high molecular weight melanoma antigen (Natali et al., 1987, Cancer 59:55-63). These publications are all incorporated herein by reference.

It will be obvious to one or ordinary skill in the art that positive control cell lines are necessary in an initial evaluation for amplifying target genes. For the study of any particular carcinoma, numerous cell lines are described in the literature and available through the ATCC Culture Collection. In the disclosed examples of the invention for detecting metastatic disease, the following cell lines are demonstrated as for positive controls: BEN/M103 (a bronchogenic lung carcinoma cell line which expresses a mixed small cell and non-small cell features and is useful as a positive control for calcitonin, chromogranin A, and PRH); NCI-H69 (expresses KS¼, bombesin/GRP, L-dopa decarboxylase, and neuron specific enolase); and 727 (SCLC positive cell lines, see Minna et al. supra.).

Once target candidates are selected and appropriate primers are prepared, they are evaluated in an in vitro system as described herein. Various concentrations of positive control characterized carcinoma cell lines are added to either peripheral blood, bone marrow samples, or hematopoietic cell lines to determine the limits of carcinoma detection for each primer pair. Table 1 provides PCR primer pairs for amplifying carcinoma metastases in hematopoietic tissues. Table 1 also includes oligonucleotide probes for detecting the amplification products.

TABLE 1

| Primer | Seq. ID No. | Sequence | Target | PCR Product Size |
|---|---|---|---|---|
| CM58 | 1 | 5'GGTGCAGGACTATGTGCAGATG | Calcitonin/CGRP | |
| CM59 | 2 | 5'GTCGCTGGACATATCCCTTTTC | Calcitonin | CM58/59–214 bp SEQ ID Nos. 1 and 2 |
| CM60 | 3 | 5'GGTGGGCACAAAGTTGTTCTTC | CGRP | CM58/60–175 bp SEQ ID Nos. 1 and 3 |
| CM63 | 4 | 5'GTTGAGGTCATCTCCGACACAC | Chromo A | — |
| CM64 | 5 | 5'CTCTGGTTCTCAAGAACCTCTG | Chromo A | CM63/64–227 bp SEQ ID Nos. 4 and 5 |
| CM65 | 6 | 5'CATCCTTGGATGATGGCTCTTC | Chromo A | CM63/65–277 bp SEQ ID Nos. 4 and 6 |
| CM67 | 7 | 5'GACCGTGCTGACCAAGATGTAC | GRP | — |
| CM68 | 8 | 5'GGTGGTTTCTGTTCTCCTTTGC | GRP | CM67/68–198 bp SEQ ID Nos. 7 and 8 |
| CM69 | 9 | 5'GAACCTGGAGCAGAGAGTCTAC | GRP | CM67/69–316 bp SEQ ID Nos. 7 and 9 |
| CM71 | 10 | 5'GTCTGTGAAAACTACAAGCTGG | KS1/4 | — |
| CM72 | 11 | 5'CCCTTCAGGTTTTGCTCTTCTC | KS1/4 | CM71/72–177 bp SEQ ID Nos. 10 and 11 |
| CM73 | 12 | 5'GTCCTTGTCTGTTCTTCTGACC | KS1/4 | CM71/73–309 bp SEQ ID Nos. 10 and 12 |
| CM75 | 13 | 5'CCGCGTGCTACTTCCAGAACTG | Neuro II | — |
| CM76 | 14 | 5'CAGGTAGTTCTCCTCCTGGCAG | Neuro II | CM75/76–191 bp SEQ ID Nos. 13 and 14 |
| CM77 | 15 | 5'GCTCTCGTCGTTGCAGCAAACG | Neuro II | CM75/77–275 bp SEQ ID Nos. 13 and 15 |
| CM79 | 16 | 5'GCTTTGTGAAGGTGCTGCAATG | Synapto | — |
| CM80 | 17 | 5'GTACTCGAACTCGACCTCGATG | Synapto | CM79/80–140 bp SEQ ID Nos. 16 and 17 |
| CM81 | 18 | 5'GACAAAGAATTCGGCTGACGAG | Synapto | CM79/81–245 bp SEQ ID Nos. 16 and 18 |
| CM61 | 19 | 5'CTGAGTACTTGCATGCTGGG | Calcitonin | |
| CM62 | 20 | 5'GACACTGCCACCTGTGTGAC | CGRP | |
| CM66 | 21 | 5'GACACTCCGAGGAQATGAAC | Chromo A | |
| CM70 | 22 | 5'CACAGGGGAGTCTTCTTCTG | GRP | |
| CM74 | 23 | 5'CTGGCTGCCAAATGTTTGGTG | KS1/4 | |
| CM78 | 24 | 5'GACCTGGAGCTGAGACAGTG | Neuro II | |
| CM82 | 25 | 5'CCAACAAGACCGAGAGTGAC | Synapto | |

For convenience probes may be synthesized biotinylated at their 5' ends so that they can be used with strepavidiniperoxidase or phosphatase type luminescent or color detection systems, for example, by TNB as described herein.

Following amplification, the reaction mixture for each sample is analyzed to determine whether or not amplification has occurred. For example, the amplification mixture may be analyzed by gel electrophoresis and ethidium bromide staining. Alternatively, oligonucleotide probes specific for each PCR product may be used in the southern blot procedure or dot assay to further increase the specificity and sensitivity of the procedure (see Sambrook et al., supra.).

Detection of the amplified products can be accomplished by a number of known means. Such means include, but are not limited to, hybridization with isotopic or non-isotopically labeled probes in, for example, a dot blot or electrophoretic format. A detection format system may include a capture step, such as a solid support substrate and avidin-biotin label system (see, for example, copending U.S. Ser. No. 690,720, filed Apr. 24, 1991,which is incorporated herein by reference). European Patent Publication No. 237, 362, which is incorporated herein by reference, also describes a PCR-based detection method termed "reverse" dot-blot in which the probe, instead of the amplified DNA, is fixed to the membrane. According to the method, the target, rather than the probe, is labeled for hybridization.

U.S. Pat. No. 5,210,015, incorporated herein by reference, describes a method for use of the 5' to 3' nuclease activity of a nucleic acid polymerase. According to the method, a labeled nucleic acid probe in a hybridized duplex composed of a labeled oligonucleotide and a target oligonucleotide is degraded. Labeled fragments are subsequently detected. Detection may also include quantitative analysis to monitor progress of, for example, an infection or response to a treatment regimen.

There are a number of ways to determine whether a probe has hybridized to a DNA sequence contained in a sample. Typically, the probe is labeled in a detectable manner. The target DNA (i.e., the amplified DNA in the PCR-reaction buffer) is bound to a solid support, and determination of whether hybridization has occurred involves determining whether the label is present on the solid support. This procedure can be varied, however, and is possible when the target is labeled and the probe is bound to the solid support. See, for example, copending Ser. No. 347,495, filed May 4, 1989, now abandoned, which is incorporated herein by reference.

Many methods for labeling nucleic acids, whether probe or target, are known in the art and are suitable for purposes of the present invention. Suitable labels may provide signals detectable by fluorescence, radioactivity, colorimetry, X-ray diffraction or absorption, magnetism, enzymatic activity, and the like. Suitable labels include fluorophores, chromophores, radioactive isotopes (particularly $^{32}$P and $^{125}$I), electrondense reagents, enzymes and ligands having specific binding partners. Enzymes are typically detected by their activity. For example, horse-radish-peroxidase (HRP) can be detected by its ability to convert diaminobenzidine to a blue pigment. A preferred method for HRP-based detection uses tetramethyl-benzidine (TMB) as described in *Clin.*

Chem. 33:1368 (1987). An alternative detection system is the Enhanced Chemiluminescent (ECL) detection kit commercially available from Amersham. The kit is used in accordance with the manufacturer's directions.

Copending U.S. Ser. No. 695,201, filed May 2, 1991, is incorporated herein by reference and describes a method for detecting amplified nucleic acids without the use of a probe. The homogeneous assay system requires that amplification occurs in the presence of a detectable DNA binding agent, for example, ethidium bromide. The fluorescence of the amplification mixture increases as the target is amplified and the amount of double-stranded DNA present in the reaction mixture increases.

In another aspect of the present invention, carcinoma metastases in selected body tissues and fluids are detected by combining the advantages of immunocytology and nucleic acid amplification technologies. In this approach, monoclonal antibodies specific for carcinoma antigens that are not expressed by the malignant cells normally present in the selected body tissue or fluid are attached to immunomagnetic beads by standard methods (Lea et al., 1986, *Scand. J. Immunol.* 23:509, and Lea et al., 1988, *J. Mol. Recogn.* 1:9). The immunomagnetic beads are then incubated with cells obtained from the selected body tissue or fluid samples. Standard magnetic separations techniques as described in Lea et al., 1986, and 1989 supra., are used to enrich the sample for carcinoma cells expressing the target antigens. The separated magnetic beads and attached carcinoma cells are place in appropriate extraction buffers to isolate RNA. The extracted nucleic acids are then utilized in appropriate nucleic acid amplification assays to detect carcinoma associated mRNA.

Immunomagnetic enrichment of the tumor cell population enhances the sensitivity of nucleic acid amplification assays, by increasing the proportion of target nucleic acid sequences in the starting reaction mixture. In one embodiment of this enrichment method, useful for detecting lung carcinomas, commercially available magnetic beads are coated with sheep anti-mouse immnunoglobulin (Dynabeads M450, Dynal Corporation) and incubated respectively with EA-1 (anti-NSCLC) and NCAM (anti-SCLC) specific monoclonal antibodies (10 µg antibody per mg particle overnight at 4° C). The antibody coated beads are then washed five times in phosphate buffered saline (PBS) containing 0.5% bovine serum albumin (BSA). The immunomagnetic beads are then suspended into 2 mils of BSA with 0.1% BSA and 0.01% $NaN_3$. To detect carcinoma cells in bone marrow of peripheral blood, ficoll-hypaque purified mononuclear cells from bone marrow or peripheral blood specimens are mixed with the immunomagnetic beads at a ratio of 1:10 in a T75 flask containing 25 mls of RMPI 1640 media with 0.01% EDTA. The cells and immunomagnetic beads are incubated overnight on a rocker platform at 4° C. The flask is then place on a soft iron plate with 10 samarium cobalt magnets for 5 minutes.

Cells attached to the immunomagnetic beads adhere to the flask bottom exposed to the magnets. Non-adherent cells are decanted from the flask. The remaining cells are then resuspended in RMPI 1640 media, and the process is repeated 5 times to further remove non-adherent cells. The immunomagnetic beads and attached cells are incubated with standard cell lysis buffers to extract total RNA and DNA. The extracted RNA and DNA is utilized in PCR assays described above to detect carcinoma associated RNA.

The present methods for detecting carcinoma metastases in hematopoietic tissues are approximately 1,000 fold more sensitive than prior conventional diagnostic methods. Consequently, the utility of these methods for disease diagnosis and intervention is considerable. For example, evaluation of peripheral blood or bone marrow specimens examined at the time of diagnosis and following initial therapy identifies patients with "localized" disease by conventional staging criteria, that have "systemic" disease based on the detection of amplified carcinoma associated RNA sequences. In addition, it is likely that many patients with "complete remissions" by conventional diagnostic methods have evidence of disease activity by the present methods. MRD detection by the methods is evaluated in connection with the clinical course of disease in patients. In general, specimens are evaluated at the time of diagnosis, upon completion of initial therapy, at six month intervals during clinically disease-free follow up and at clinically revert relapse. MRD detection by the disclosed invention is correlated with the duration of disease-free survival (assessed by conventional methods) and with overall survival. In addition, the present methods are useful for detecting MRD in bone marrow autographs utilized in autologous bone marrow transplantation therapies for carcinomas. The present methods are useful for evaluating the adequacy of methods to remove residual tumor cells from the marrow prior to transplantation and identify bone marrows best suited for this form of cancer therapy.

In another aspect, the present invention can be provided in a kit format for detecting metastatic carcinomas in selected body tissues and fluids. Such a kit includes a primer pair for amplifying a target carcinoma associated nucleic acid sequence, which sequence is preferentially expressed in carcinoma cells and is not expressed by original resident cells present in the selected body tissue or fluid tissues. Kits may also include any of the following: a probe for detecting the presence of the amplified target, an enzyme for reverse transcribing RNA to provide cDNA, a DNA polymerase for amplifying the target cDNA, appropriate amplification buffers and deoxyribonucleoside triphosphates.

EXAMPLE 1

Presence of Target Carcinoma Associated mRNA in Representative Tumor Cells

The RNA PCR primers described in Table 1 were used to demonstrate the feasibility of using PCR analysis of gene expression to detect lung cancer metastases. The expected size PCR products for each primer pair are also described in Table 1. The carcinoma samples utilized were the following: cell line 478 (SCLC cell line) approximately $15 \times 10^6$ cells, M103 (lung carcinoma cell line) approximately $25 \times 10^6$ cells, and bone marrow ([All] acute lymphocytic leukemia patient).

RNA was isolated by the RNAZOL method described in Chomczynski and Sacchi, supra, in a kit format purchased from Cinna/Biotecx Labs Inc., Friendswood, Tex. RNA was reprecipitated twice from ethanol and dissolved in TE (10 mM Tris HCl pH 7.5, 1 mM EDTA by heating at 95° C. for 10 minutes). Sample M103 contained large amounts of DNA precipitate and was treated with 10 units of DNase (RNase-free DNase from Boheringer, Mannheim) and 500 µl PCR buffer (50 mM KCl, 20 mM Tris-HCl, pH 8.4, 2.5 mM $MgCl_2$) for 30 minutes at 37° C. The sample was extracted twice with phenol chloroform and precipitated three times with ethanol and dissolved in TE by heating at 95° C. for 10 minutes. The RNA solutions were diluted and absorbance at 260 nM was determined to calculate the nucleic acid concentration for each sample. The cell line 478 sample contained 81.6 µg in 200 µl; (408 µg/ml). M103 sample contained 598 μg in 500 μl (1.2 μg/ml), and the bone marrow sample contained 83.2 μg in 400 μl (208 μg/ml).

Reverse Transcriptase Reactions

A reverse transcription (RT) master mix was prepared for 30 reactions at 20 μl per reaction. The RT master mix contained 60 μl of 10× PCR buffer (1× buffer is 50 mM KCl, 20 mM Tris-HCl, pH 8.4 2.5 mM MgCl$_2$), 405 μl of sterile distilled H$_2$O, 60 μl of 10 mM DNTP, 15 μl of RNasin (Promega 40 units/μl), 30 μl of EK293 (100 pmol per μl), and 30 μl of reverse transcriptase (BRL 200 units/μl). EK293 is a mixture of random hexadeoxyribonucleotides for priming cDNA as described in Feinberg and Vogelstein, 1984, *Anal. Biochem.* 137:266–267.

Random hexadeoxy-ribonucleotides are commercially available from Promega, Madison, Wis. For each sample 200 μl of the RT master mix was added to RNA as follows: 478, 10 μl RNA; M103, 5 μl of RNA; and bone marrow, 20 μl of RNA. TE was added for a final volume of 220 μl.

Each reaction was left at room temperature for 15 minutes and then incubated at 45° C. for 30 minutes. Ten to twenty μl was removed for PCR.

PCR Reactions

A PCR master mix for 30 reactions was prepared as follows. Two hundred and seventy μl of 10× PCR buffer, 2424 μl of sterile distilled H$_2$O, and 6 μl (5 units per μl, PECI) of Taq polymerase were combined. For each PCR reaction, 100 μl of mineral oil was overlayed on top of the reaction. Reactions were set up as follows.

TABLE 2

| Tube No. | Target | Primers | SEQ ID Nos. | Product Size |
|---|---|---|---|---|
| 1, 10, 19 | Calcitonin | CM58/59 | 1 and 2 | 214 bp |
| 2, 11, 20 | CGRP | CM58/60 | 1 and 3 | 75 bp |
| 3, 12, 21 | Chrome A | CM63/64 | 4 and 5 | 227 bp |
| 4, 13, 22 | GRP | CM67/68 | 7 and 8 | 198 bp |
| 5, 14, 23 | KS1/4 | CM71/72 | 10 and 11 | 177 bp |
| 6, 15, 24 | Neuro II | CM75/76 | 13 and 14 | 191 bp |
| 7, 16, 25 | Synapto | CM79/80 | 16 and 17 | 120 bp |
| 8, 17, 26 | β-actin | EK169/170 | 26 and 27 | 243 bp |
| 9, 18, 27 | — | No Primer | — | — |

Tube Nos. 1–9 contained cell line 478 cDNA. Tube Nos. 10–18 contained cell line M103 cDNA. Tube Nos. 19–27 contained bone marrow cDNA. For each reaction, 10 μl of cDNA and 90 μl of PCR master mix were used. For each amplification reaction 25 pmols of each primer was included. β-actin was included as a positive control, and the "no primer" samples served as negative controls.

For PCR, the samples were heat denatured at 95° C. for 2 minutes and then 35 PCR cycles were run. The thermocycling profile was as follows: 94° C. for 1 minute, 1 minute ramp to 55° C., 55° C. for 1 minute, 30 second ramp to 72° C. for 30 seconds, 30 second ramp to 94° C. After 35 cycles a 10 minute 72° C. extension step was included and reactions were chilled at 15° C. Each reaction was extracted once with 200 μl of TE saturated chloroform. Five μl were analyzed on a 2% NuSeive—1% agarose composite gel and stained with ethidium bromide and photographed.

The results demonstrated that each primer pair was capable of generating a specific PCR product of the predicted size. However, not all mRNA sequences were present in each lung cancer cell line. Calcitonin was not present in the 478 line, while GRP and neurophysin appeared to be absent in the M103 cell line. In bone marrow RNA from an ALL patient none of the primers amplified a PCR product of correct size. These results demonstrate that it is not only possible to differentiate between the lung cancer cells and bone marrow, but also differentiate between different cancers by their differential expression of the various target mRNAs.

EXAMPLE 2

Absence of Target Carcinoma Associated mRNA in Representative Body Tissues or Fluids The bone marrow RNA described in Example 1 and PBL RNA were used as templates in cDNA and amplification reactions as described in Example 1 to demonstrate the suitability of the present methods on samples from patients without carcinomas. PBL RNA was prepared as described above after ficoll-hypaque separation of a bone marrow aspirate. A reverse transcriptase master mix was prepared containing 20 μl of 10× PCR buffer, 330 μl of sterile distilled H$_2$O, 20 μl of dNTPs (10 mM) 10 μl of RNasin (40 units per μl), 10 μl of EK293 (100 pmol per μl), and 10 μl reverse transcriptase (200 units per μl). For the reverse transcriptase reaction, 200 μl of RT master mix was combined with 10 μl of bone marrow RNA (208 μg/ml) or PBL RNA (320 ug/ml). The reactions were incubated at room temperature for 15 minutes and then 45° C. for 30 minutes. Reverse transcriptase was then heat killed by incubating reactions at 95° C. for 10 minutes. Ten μl of the reverse transcriptase reactions were used for PCR.

Amplification Reactions

A PCR master mix was prepared containing 180 μl of 10× PCR buffer, 1615 μl of sterile distilled water and 5 μl of a polymerase (25 units). Ninety microliters of the PCR master mix was aliquoted into PCR tubes. One microliter of each primer (25 pmols each) and a 10 μl cDNA was added to each tube as follows.

TABLE 3

| Tube No. | Target | RNA Sample | Primers | SEQ ID Nos. |
|---|---|---|---|---|
| 1a | Calcitonin | bone marrow | CM58/59 | 1 and 2 |
| 1b | Calcitonin | PBL | CM58/59 | 1 and 2 |
| 2a | CGRP | bone marrow | CM58/60 | 1 and 3 |
| 2b | CGRP | PBL | CM58/60 | 1 and 3 |
| 3a | Chromo A | bone marrow | CM63/64 | 4 and 5 |
| 3b | Chromo A | PBL | CM63/64 | 4 and 5 |
| 4a | GRP | bone marrow | CM67/68 | 7 and 8 |
| 4b | GRP | PBL | CM67/68 | 7 and 8 |
| 5a | KS1/4 | bone marrow | CM71/72 | 10 and 11 |
| 5b | KS1/4 | PBL | CM71/72 | 10 and 11 |
| 6a | Neuro II | bone marrow | CM75/76 | 13 and 14 |
| 6b | Neuro II | PBL | CM75/76 | 13 and 14 |
| 7a | Synapto | bone marrow | CM79/80 | 16 and 17 |
| 7b | Synapto | PBL | CM79/80 | 16 and 17 |
| 8a | β-actin | bone marrow | AW75/76 | 30 and 31 |
| 8b | β-actin | PBL | AW75/76 | 30 and 31 |
| 9a | no primers | bone marrow | — | — |
| 9b | no primers | PBL | — | — |

The PCR reactions were heated at 95° C. for two minutes and then subjected to 35 amplification cycles using the following thermocycling parameters: 94° C. for 1 minute, then a 1 minute ramp to 55° C. for 30 seconds, a 30 second ramp, 72° C. for 30 seconds and a 30 second ramp to 94° C. Following amplification the reactions were allowed to extend to 10 minutes at 72° C. and then chilled on ice. Each reaction was extracted with 200 μl of chloroform and analyzed by gel electrophoresis and ethidium bromide staining.

Gel analysis indicated that by ethidium bromide staining, normal PBL RNA and leukemia bone marrow samples do not contain any of the lung cancer RNAs. A band slightly smaller and one slightly larger then the expect sized mRNA band for GRP amplification did appear in the PBL RNA sample. However, no bands of the predicted PCR size products were apparent in these negative control samples.

EXAMPLE 3

Screening for Pseudogenes

The experiment described in Example 1 was repeated using PBL DNA to determine whether processed pseudogenes were present in the genome. DNA was isolated from ficoll-hypaque purified mononuclear cells by standard methods (Sambrook et al. supra.). Consequently, the reverse transcriptase step was omitted. This analysis also served to determine whether or not genomic DNA sequences would be amplified that would interfere with the desired analysis. The reactions were set up as follows:

TABLE 4

| Tube No. | Target | Primers | SEQ ID Nos. |
|---|---|---|---|
| 1, 2 | Calcitonin | CM58/59 | 1 and 2 |
| 3, 4 | CGRP | CM58/60 | 1 and 3 |
| 5, 6 | Chromo A | CM63/64 | 4 and 5 |
| 7, 8 | GRP | CM67/68 | 7 and 8 |
| 9, 10 | KS1/4 | CM71/72 | 10 and 11 |
| 11, 12 | Neuro II | CM75/76 | 13 and 14 |
| 13, 14 | Synapto | CM79/80 | 16 and 17 |
| 15, 16 | β-actin | EK169/170 | 26 and 27 |
| 17, 18 | — | No Primers | — |

The reactions were run in 100 µl of 1× PCR buffer containing 100 ng of PBL DNA, 0.1 mM dNTPs, 25 pmol of each primer and 1.25 units Taq polymerase. One hundred microliters of mineral oil was overlayed onto each PCR reaction to prevent evaporation. The reactions were heated to 95° C. for 2 minutes and then 35 cycles as described in Example 1. Following the amplification, the reactions extracted with chloroform and 5 µl of each was analyzed by gel electrophoresis as described in Example 1. Tube Nos. 15–18 served as positive and negative controls as in Example 1.

The results demonstrated that none of the primer pairs tested amplified a predicted mRNA sized band as specified in Table 1. Thus, no closely related processed pseudogenes were present for any of the targeted genes. Therefore, contaminating genomic DNA does not interfere with this assay.

EXAMPLE 4

Sensitivity Analysis

Two cell lines, a positive control and a negative control, were used in a mixing experiment to ascertain the sensitivity of the present methods. Cell line 8402, a T-cell line, and cell line 727, a small cell lung carcinoma cell line, served as the negative and positive cell samples. Cells from 727 were diluted into 8402 in the following proportions: 1:100; 1:1, 000; 1:10,000; and 1:100,000. Each dilution contained 2×10$^6$ 8402 cells plus 727 cells in the approximately designated proportion; i.e., at 1:100,000 there were twenty-eight 727 cells plus 2 million 8402 cells. RNA was then isolated according to Chomczynski and Sacchi, supra.

RNA-PCR was done as described in the previous examples using the KS¼ primer pair CM71/72 (SEQ ID NOS. 10 and 11). One µg RNA was used in each RT reaction. The entire RT reaction was used in the PCR step. The cycling parameters were: 95° C. for 1 minute, 55° C. for 1 minute 73° C. for 2 minutes, for 35 cycles and 72° C. for 10 minutes at the end of PCR. The PCR products were analyzed (20 µl of the 100 µl PCR reaction) on a 1% agarose gel, stained with ethidium bromide and photographed.

All dilutions were positive for the 177 base pair band expected, including the 1:10$^5$ reaction. The T-cell line without any 727 cells added in was included as a negative control, and no PCR product was detected. However, as positive controls, C-ABL RNA was amplified in both 727 and 8402 cells and demonstrated competency of the samples.

Thus, this experiment showed that KS¼ mRNA was detected in 1 µg RNA from a 1 to 100,000 dilution of positive cells.

EXAMPLE 5

Evaluation of Bone Marrow and PBLs from Normal and Leukemic Patients With and Without Cervical Cancer This experiment compared amplification of target gene sequences using PBL RNA isolated from an ALL patient and from a normal patient. The reactions also included two bone marrow samples which comprised the bone marrow sample described in Example 1 and a bone marrow sample isolated from an additional ALL patient. Thus, the samples were as follows: PBL No. 1 was from a normal individual and contained 320 ug RNA per ml; PBL No. 2 was RNA from an ALL individual and contained 560 µg RNA per ml; Bone Marrow No. 1 was also from an ALL individual and contained 208 µg RNA/ml; Bone Marrow No. 2 was from the same ALL individual as PBL No. 2 and the RNA concentration was not determined. The medical bone marrow No. 1, ALL patient indicated that the patient also suffered cancer. RNA was prepared as described in the previous examples.

Reverse Transcription Reactions

For the reverse transcription reactions, a master mix was prepared containing 80 µl of 10× PCR buffer, 560 µl of sterile distilled H$_2$O, 80 µl of 10 mM dNTP, 20 µl of RNasin (40 units per µl), 40 µl of EK293 (100 pmols per µl), and 20 µl of reverse transcriptase (200 units per µl Betheda Research Labs). For each RNA sample 180 µl of the RT master mix was added to RNA as follows: PBL No. 1 RNA 18 µl, PBL No. 2 RNA 9 µl, Bone Marrow No. 1 RNA 9 µl, and Bone Marrow No. 2 RNA 36 µl. Each RT reaction was made up to a final volume of 216 µl with TE. The reactions were incubated at room temperature for 10 minutes, then at 45° C. for 30 minutes. The enzyme was heated killed at 99° C. for 5 minutes, and then the reactions were chilled.

Amplification Reactions

For PCR a master mix was prepared containing 400 µl of 10× PCR buffer, 3,590 µl of sterile distilled H$_2$O, and 10 µl of Taq polymerase (5 units per µl). For each reaction, 90 µl of PCR master mix, 1 µl of each primer pair (25 pmol/µl) and 10 µl cDNA reaction were mixed. Nine PCR reactions for each of the four cDNA reactions were set up as follows.

TABLE 5

| Reaction No. | Target | Primers | SEQ ID Nos. | Predicted Product Size |
|---|---|---|---|---|
| 1 | Calcitonin | CM58/59 | 1 and 2 | 214 bp |
| 2 | CGRP | CM58/60 | 1 and 3 | 175 bp |
| 3 | Chromo A | CM63/64 | 4 and 5 | 227 bp |
| 4 | GRP | CM67/68 | 7 and 8 | 198 bp |
| 5 | KS1-4 | CM71/72 | 10 and 11 | 177 bp |

TABLE 5-continued

| Reaction No. | Target | Primers | SEQ ID Nos. | Predicted Product Size |
|---|---|---|---|---|
| 6 | Neuro | CM75/76 | 13 and 14 | 191 bp |
| 7 | Synapto | CM79/80 | 16 and 17 | 120 bp |
| 8 | C-ABL | EK405/407 | 28 and 29 | 377 bp |
| 9 | — | No Primers | — | |

EK 405/407 (SEQ ID NOS. 28 and 29) are C-ABL primers used as a control to show that the RNA sample is undegraded. If EK405/407 (SEQ ID NOS. 28 and 29) PCR is negative, then the sample is not reliable.

The PCR reactions were conducted as described in Example 3 and the results analyzed by electrophoresis and ethidium bromide staining. In PBL Nos. 1 and 2 none of the lung-specific mRNAs were detected in either the normal or the ALL patient samples. The analysis of the Bone Marrow No. 2 sample, from an ALL patient was negative. None of the lung-specific mRNs were amplified and detected. However, the analysis of sample Bone Marrow No. 1 from an ALL patient who also had cervical cancer was positive for all target tested with the exception of Neuro II and GRP. The presence of the predicted sized bands in this sample suggested that the cervical cancer had metastasized.

We claim:

1. A method for detecting metastasis of a carcinoma in a human, wherein said method comprises:

(a) treating a sample of non-epithelial non-edocrine body tissue or fluid under conditions for amplifying a target mRNA sequence, wherein said target mRNA sequence is expressed in healthy and malignant epithelial or endocrine cells, and wherein said target mRNA sequence is not expressed in healthy cells present in said sample body tissue or fluid; and (b) determining if amplification of said target mRNA sequence has occurred, which indicates metastasis of said carcinoma.

2. The method of claim 1, wherein said conditions for amplifying a target mRNA sequence comprise firstly treating said sample under conditions for reverse transcribing said target mRNA sequence to provide a cDNA, and secondly treating said sample under conditions for amplifying said cDNA using a polymerase chain reaction.

3. The method of claim 2, wherein said body tissue or fluid is selected from the group consisting of bone marrow aspirates, bone marrow biopsies, peripheral blood, lymph node aspirates, lymph node biopsies, ascites, pleural effusions, and cerebrospinal fluid.

4. A method for monitoring minimal residual disease in a patient following treatment for prostate carcinoma, wherein said method comprises:

(a) carrying out the method of claim 1 following treatment; and (b) carrying out the method of claim 1 at 6 month intervals following step (a) during clinically disease-free follow-up.

5. A method for detecting minimal residual disease in human bone marrow prior to autologous bone marrow transplautation therapy, wherein said method comprises:

(a) treating a sample of said bone marrow, wherein said bone marrow has been treated with a method to remove malignant epithelial or endocrine cells, under conditions for amplifying a target mRNA sequence, wherein said target mRNA sequence is expresed in healthy and malignant epithelial or endocrine cells, and wherein said target mRNA sequence is not expressed in healthy bone marrow cells;

(b) determining if amplification of said target mRNA sequence has occurred, thereby determining if residual malignant epithelial or endocrine cells are present, which indicates residual disease.

\* \* \* \* \*